(12) United States Patent  
Napier et al.

(10) Patent No.: US 7,868,017 B2  
(45) Date of Patent: Jan. 11, 2011

(54) 9-AZABICYCLO[3.3.1]NONANE DERIVATIVES

(75) Inventors: Susan Elizabeth Napier, Newhouse (GB); Matilda Jane Bingham, Newhouse (GB); Margaret Jean Huggett, Newhouse (GB); Mark Huggett, Newhouse (GB); Yasuko Kiyoi, Newhouse (GB); Olaf Nimz, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/541,273

(22) Filed: Sep. 29, 2006

(65) Prior Publication Data

US 2007/0112019 A1   May 17, 2007

Related U.S. Application Data

(60) Provisional application No. 60/721,964, filed on Sep. 30, 2005.

(51) Int. Cl.  
*A01N 43/42* (2006.01)  
*A61K 31/44* (2006.01)  
*C07D 221/02* (2006.01)

(52) U.S. Cl. ........................ 514/299; 544/183
(58) Field of Classification Search ............... 546/183; 514/299  
See application file for complete search history.

(56) References Cited

U.S. PATENT DOCUMENTS

| 5,958,945 | A | 9/1999 | Imbert et al. |
| 7,199,147 | B2 | 4/2007 | Imazaki et al. |

FOREIGN PATENT DOCUMENTS

| EP | 1 403 255 A1 | 3/2004 |
| GB | 1 164 555 A | 9/1969 |
| JP | 04 208267 A | 7/1992 |
| JP | 3087763 | * 7/1992 |
| JP | 3087763 | 7/2000 |
| WO | WO 02/100833 | 12/2002 |
| WO | WO 03/062235 | 7/2003 |
| WO | WO 2004/043904 | 5/2004 |
| WO | WO 2004/113334 | 12/2004 |
| WO | 2005/123728 | * 6/2005 |
| WO | WO 2005/123728 | 12/2005 |
| WO | WO 2005/123728 A1 | 12/2005 |

OTHER PUBLICATIONS

Arvanitis, et al., "Imidazo[4,5-b]pyridines as Corticotropin Releasing Factor Receptor Ligands," *Bioorg. Med. Chem. Lett.* 13 (2003) 125-128.

Batt, et al., "Regioselectivity in the Acid-Catalyzed Isomerization of 2-Substituted 1,4-Dihydro-1,4-epoxynaphthaleness," *J. Org. Chem.* 56(23) (1991) 6704-6708.

Bell, et al., "Regioselective Monomethylation of Unsymmetrical Naphthalenediols with Methanolic HCl," *Aust. J. Chem.* 46(5) (1993) 731-737.

Boxhall, et al., "The Desymmetrisation of Resorcinol: The Synthesis of Resorcinol Monoalkyl Ethers", *Synlett.* 7(2003) 997-1001.

Castro, et al., "Mitsunobu-like Processes with a Novel Triphenylphosphine-Cyclic Sulfamide Betaine," *J. Org. Chem.* 59 (1994) 2289-2291.

de Lang, et al., "Transition Metal Catalysed Cross-Coupling Between Benzylic Halides and Aryl Nucleophiles. Synthesis of some Toxicologically Interesting Tetrachlorobenzyltoluenes," *Tetrahedron* 54(12) (1998) 2953-2966.

Den Hertog, et al., "The Chloropyridines" *Recl. Trav. Chim. Pays-Bas* 69 (1950) 673-699.

Hulme, et al. "Asymmetric Synthesis of the Key Intermediates Leading to (-)-Aphanorphine and (-)-Eptazocine," *J. Org. Chem.* 60(5) (1995) 1265-1270.

Ito et al., "A New Preparation fo Benzofuran Utilizing Trimethylsilyldiazomethane," *Synlett* 10 (1997) 1163-1164.

Kolder, et al., "Synthesis and Reactivity of 5-Chloro-2,4-Dihydroxypyridine," *Recl. Tray. Chim. Pays-Bas* 72 (1953) 285-295.

Kraiss, et al., "Chemistry of Tropan-3-yl Ethers. Part I. Synthesis of Tropan-3-yl Ethers," *J. Chem. Soc., Phys. Org.* 11 (1971) 2145-2149.

Momose et al., "Bicyclo[3.3.1]nonanes as synthetic intermediates. Part 19. Asymmetric cleavage of ω-azabicyclo[3.n.1]alkan-3-ones at the 'fork head'," *J. Chem. Soc., Perkins Trans.* 1, (1997) 1307-1313.

Mukherjee et al., "Studies in Sulfur Heterocycles. Part 8. 3,4-Dihydro-thieno[2,3-i][1]benzoxepin-5(2H)-one, a New Heterocyclic System and a Key Intermediate in the Synthesis of Novel Polycondensed Sulfur Heterocycles," *J. Chem. Res.* (1993) 192-193.

(Continued)

*Primary Examiner*—D. Margaret Seaman  
*Assistant Examiner*—Niloofar Rahmani  
(74) *Attorney, Agent, or Firm*—Susan L. Hess

(57) ABSTRACT

The present invention relates to a 9-azabicyclo[3.3.1]nonane derivative of formula I,

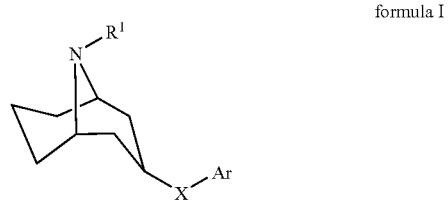

formula I wherein each of the substituents is given the definition as set forth in the specification and claims, or a pharmaceutically acceptable salt or solvate thereof. The invention also relates to pharmaceutical compositions comprising said 9-azabicyclo [3.3.1]nonane derivatives and to their use in therapy.

8 Claims, No Drawings

OTHER PUBLICATIONS

Oberhauser, "A New Bromination Method for Phenols and Anisoles: NBS/HBF$_4$,Et$_2$O in CH$_3$CN," *J. Org. Chem.* 62 (1997) 4504-4506.

Rahman, et al., "7-Substituted Benzo[*b*]thiophenes and 1,2-Benzisothiazoles. Part I .Hydroxy-or Methoxy-derivatives," *J. Chem. Soc.* (*Perkin Trans. 1*) (1983) 2973-2977.

Zambias et al., "The Synthesis of 5-Hydroxy-2,3-Dihydrobenzo(B)Thiophene (1) Via an Efficient One Step Preparation of 5-Nitro-Benzo(B)Thiophene-2-Carboxylate (3A)," *Synth. Comm.* 21(7) (1991) 959-964.

Ananthan, Subramaniam, et. al.; "Identification of a novel partial inhibitor of dopamine transporter among 4-substituted 2-phenylquinazolines,". Bioorganic & Medicinal Chemistry Letters; 12 (16); pp. 2225-2228, (2002).

Derwent Publications, Ltd. London, GB, AN 1992—303575; XP 002361888 Abstract.

Patent Abstracts of Japan, vol. 016, No. 544 (C-1004), Nov. 13, 1992.

International Search Report for PCT/EP2006/066896 mailed Jul. 11, 2006.

Written Opinion for International Application No. PCT/EP2006/066896 mailed on Jul. 11, 2006.

International Search Report for PCT/EP2006/069047 mailed Mar. 15, 2007.

Written Opinion for International Application No. PCT/EP2006/069047 mailed Mar. 15, 2007.

* cited by examiner

9-AZABICYCLO[3.3.1]NONANE DERIVATIVES

The present invention relates to a 9-azabicyclo[3.3.1] nonane derivative, to a pharmaceutical compositions comprising said compound and to its use in therapy, in particular to its use for the treatment or prevention of a disease or disorder for which the reuptake inhibition of one or more monoamine neurotransmitter contributes to the therapeutic effect.

Monoamine reuptake inhibitors have found widespread use in therapy, in particular, in the treatment of depression, a common, serious and life-threatening disorder with persistent and debilitating side-effects. The older tricyclic monoamine reuptake inhibitors, including imipramine and amitriptyline are effective antidepressants but these compounds additionally have deleterious cardiovascular and anticholinergic side-effects which can lead to serious toxicity in overdose and to poor patient compliance. The newer drugs, such as the selective serotonin reuptake inhibitors (SSRIs), whilst being an improvement over older antidepressants have their own particular pattern of side-effects which include sleep disturbances, gastrointestinal symptoms and sexual problems. Monoamine reuptake inhibitors are also indicated to be useful in the treatment of other disorders such as pain, panic disorders and obsessive compulsive disorder.

In view of the shortcomings of the currently available monoamine reuptake inhibitors, the search for new compounds which are safe and effective continues. In particular, recently, there has been renewed interest in a group of drugs which in addition to inhibiting the reuptake of serotonin, also inhibit the reuptake of noradrenaline and dopamine.

WO 04/113334 discloses 8-azabicyclo[3.2.1]octane derivatives indicated to be monoamine neurotransmitter reuptake inhibitors and as such useful in the treatment of diseases or disorders responsive to inhibition of monoamine neurotransmitter reuptake in the central nervous system. WO 04/113334 however does not disclose ring systems apart from 8-azabicyclo[3.2.1]octane.

WO 03/062235 discloses thio-bridged aryl compounds, including 3-arylthio-9-azabicyclo[3.3.1]nonane derivatives, indicated to be modulators of acetylcholine receptors and as such, useful for the treatment of dysfunctions of the central and autonomic nervous system. WO 03/062235 however does not disclose 3-aryloxo-9-azabicyclo[3.3.1]nonane derivatives or 3-arylamino-9-azabicyclo[3.3.1]nonane derivatives.

WO 02/100833 discloses heterocyclic compounds indicated to be useful as therapeutic agents for diseases for which Rho kinase is responsible. There is no suggestion, however, that the compounds disclosed in WO 02/100833 would be useful for the manufacture of a medicament for the treatment or prevention of a disease or disorder for which the reuptake inhibition of one or more monoamine neurotransmitter contributes to the therapeutic effect.

The synthesis of exo-9-methyl-3-phenoxy-9-azabicyclo [3.3.1]nonane is described in J. Chem. Soc., Phys. Org., 1971, 11, 2145. No suggestion however is made in J. Chem. Soc., Phys. Org., 1971, 11, 2145 about any possible medicinal properties of said compound.

In a first aspect the present invention provides a 9-azabicyclo[3.3.1]nonane derivative of formula I

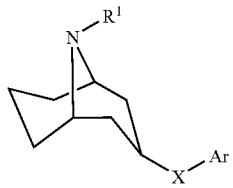

formula I wherein
$R^1$ is H or $C_{1-5}$alkyl;
X is O or $NR^2$, wherein $R^2$ is H, $C_{1-5}$alkyl or $C_{2-5}$acyl and
Ar is $C_{6-10}$aryl or a 5-10 membered heteroaryl ring system, both being optionally substituted with one to three of $R^3$-$R^5$ independently selected from halogen, $C_{1-5}$alkyl, $C_{1-5}$alkoxy, $C_{3-6}$cycloalkyl, $C_{2-5}$alkenyl, $C_{2-5}$alkynyl, CN, $NO_2$, hydroxy, phenyl, phenoxy and phenyl$C_{1-3}$alkoxy, wherein said $C_{1-5}$alkyl and $C_{1-5}$alkoxy are optionally substituted with one to three halogens and wherein said phenyl, phenoxy and phenyl$C_{1-3}$alkoxy are optionally substituted with one to three substituents independently selected from halogen and methyl or two of $R^3$-$R^5$ at adjacent positions together form a methylenedioxy or propylene unit, with the proviso that the compounds exo-9-methyl-3-phenoxy-9-azabicyclo[3.3.1]nonane and N-(9-methyl-9-azabicyclo[3.3.1]non-3-yl)-1H indazole-5-amine are excluded;

or a pharmaceutically acceptable salt or solvate thereof.

The term $C_{1-5}$alkyl, as used herein, represents a branched or unbranched alkyl group having 1-5 carbon atoms. Examples of such groups are methyl, ethyl, isopropyl, tertiary butyl and pentyl.

The term $C_{2-5}$ acyl, as used herein, represents an acyl group derived from a carboxylic acid having 2-5 carbon atoms. The acyl group can comprise a hydrocarbon which may be branched, unbranched, saturated or unsaturated. Examples of such groups include formyl, acetyl, propionyl, acryloyl and pivaloyl. Also included within the definition of $C_{2-5}$ acyl are groups derived from dicarboxylic acids like groups derived from malonic acid.

The term $C_{1-5}$alkoxy, as used herein, represents a branched or unbranched alkoxy group having 1-5 carbon atoms. Examples of such groups are methoxy, ethoxy, isopropyloxy and tertiary butyloxy.

The term $C_{3-6}$cycloalkyl, as used herein, represents a branched or unbranched cyclic alkyl group having 3-6 carbon atoms. Examples of such groups are cyclopropyl, cyclopentyl and 2-methylcyclopentyl.

The term $C_{2-5}$alkenyl, as used herein, represents a branched or unbranched alkenyl group having 2-5 carbon atoms and at least one double bond. Examples of such groups are ethenyl and propenyl.

The term $C_{2-5}$alkynyl, as used herein, represents a branched or unbranched alkynyl group having 2-5 carbon atoms and at least one triple bond. Examples of such groups are ethynyl and propynyl.

The term $C_{6-10}$aryl, as used herein, represents an aromatic group having 6-10 carbon atoms. Examples of such groups include phenyl and naphthyl.

The term 5-10 membered heteroaryl ring system, as used herein, represents a monocyclic or fused bicyclic 5-10 membered heteroaromatic ring system comprising 1-2 heteroatoms selected from N, O and S. Examples of such groups include furanyl, pyrrolyl, thienyl, pyridinyl, oxazolyl, imidazolyl, thiazolyl, pyrimidinyl, benzothienyl, quinolinyl and isoquinolinyl.

The term halogen, as used herein, represents a F, Cl, Br or I atom.

The term phenyl$C_{1-3}$alkoxy, as used herein, represents a $C_{1-3}$ alkoxy group which is substituted with a phenyl group. Examples of such groups include benzyloxy and phenethyloxy.

In one embodiment of the present invention $R^1$ is H.
In a further embodiment $R^1$ is methyl.
In another embodiment X is O.
In a further embodiment X is N-methyl.
In another embodiment Ar is phenyl or naphthyl, both being optionally substituted with one or two substituents independently selected from chloro, fluoro, methyl, trifluoromethyl and nitrile.
In a further embodiment Ar is phenyl, optionally substituted with one or two substituents independently selected from chloro, fluoro and methyl.
In a further embodiment Ar is a heteroaryl ring selected from thienyl, pyridyl, benzothienyl, benzofuranyl and benzoisothiazolyl, said heteroaryl ring being optionally substituted with one or two substituents independently selected from chloro, fluoro and methyl. In another embodiment Ar is a heteroaryl ring selected from benzothienyl, benzoisothiazolyl and pyridyl, said heteroaryl ring being optionally substituted with 1-2 substituents independently selected from chloro, fluoro and methyl.
In a further embodiment Ar is pyridyl optionally substituted with one or two chloro atoms.
In another embodiment Ar is benzothienyl optionally substituted with chloro, fluoro or methyl. In a further embodiment Ar is benzo[b]thienyl optionally substituted with chloro, fluoro or methyl.
In another embodiment Ar is benzoisothiazolyl, optionally substituted with chloro, fluoro or methyl. In a further embodiment Ar is benzo[d]isothiazolyl optionally substituted with chloro, fluoro or methyl.
In a further embodiment is a 9-azabicyclo[3.3.1]nonane derivative selected from:

exo-3-(benzo[d]isothiazol-7-yloxy)-9-azabicyclo[3.3.1]nonane;
exo-3-(benzo[d]isothiazol-4-yloxy)-9-azabicyclo[3.3.1]nonane;
exo-3-(3-chloro-2-fluorophenoxy)-9-azabicyclo[3.3.1]nonane;
exo-3-(benzo[b]thiophen-7-yloxy)-9-azabicyclo[3.3.1]nonane;
exo-3-(benzo[b]thiophen-6-yloxy)-9-azabicyclo[3.3.1]nonane;
exo-3-(benzo[b]thiophen-4-yloxy)-9-azabicyclo[3.3.1]nonane;
exo-3-(3,4-dichloropyridin-2-yloxy)-9-azabicyclo[3.3.1]nonane;
exo-3-(5,6-dichloropyridin-2-yloxy)-9-azabicyclo[3.3.1]nonane;
exo-3-(4,6-dichloropyridin-2-yloxy)-9-azabicyclo[3.3.1]nonane;
exo-3-(3-fluoro-4-methylphenoxy)-9-azabicyclo[3.3.1]nonane;
exo-3-(2,3-dichlorophenoxy)-9-azabicyclo[3.3.1]nonane;
exo-3-(9-azabicyclo[3.3.1]non-3-yloxy)benzonitrile;
exo-3-(3,5-dichlorophenoxy)-9-azabicyclo[3.3.1]nonane and exo-3-(3-prop-1-ynylphenoxy)-9-azabicyclo[3.3.1]nonane or a pharmaceutically acceptable salt or solvate thereof.

The 9-azabicyclo[3.3.1]nonane derivatives of Formula I are prepared by methods well known in the art of organic chemistry, see for example, J. March, '*Advanced Organic Chemistry*' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wuts '*Protective Groups in Organic Synthesis*' $2^{nd}$ Edition, John Wiley and Sons, 1991. The protecting groups are optionally removed at a convenient subsequent stage using methods well known in the art.

Compounds of formula I, wherein X is O can be prepared by coupling of compounds of formula II, wherein $R^1$ has the meaning as previously defined and OY represents a hydroxy or activated derivative thereof such as mesylate or tosylate, with alcohols of formula ArOH wherein Ar has the meaning as previously defined. When —OY represents a suitable leaving group (e.g. mesylate or tosylate) nucleophilic displacement can be effected with the aid of a strong organic or inorganic base such as BEMP, potassium carbonate. Additionally nucleophilic displacement can be effected using a preformed metal salt, formed by reaction of alcohols of formula ArOH with a metal hydride, for example sodium hydride. When —OY represents a hydroxy (i.e. Y=H) the substitution reaction can also be effected using the Mitsunobu reaction with the aid of coupling reagents such as diethylazodicarboxylate(DEAD) and triphenylphosphine, 1,1'-azodicarbonyldipiperidine(ADDP) and tributylphosphine or (4,4-dimethyl-1,1-dioxido-1,2,5-thiadiazolidin-2-yl)triphenylphosphonium.

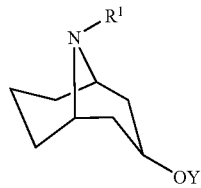

formula II

Compounds of the formula II can be prepared by literature procedures or modifications of literature procedures known to those persons skilled in the art. For example by reduction of a 9-azabicyclo[3.3.1]nona-3-one with a suitable reducing agent such as sodium borohydride in a suitable solvent such as ethanol.

Compounds of formula ArOH, wherein Ar has the meaning as previously defined, can be obtained from commercial sources, prepared by literature procedures or modifications of literature procedures known to those persons skilled in the art. For example, compounds of formula ArOH, wherein the aryl group is substituted with one or more halogens can be prepared by halogenation of the related methyl ethers (i.e. ArOMe) using procedures well known in the art followed by demethylation with, for example, pyridine hydrochloride. For example, chlorination can be accomplished using agents such as thionyl chloride, oxalyl chloride or N-chlorosuccinimide and bromination can be accomplished using phosphorous tribromide or a combination of carbon tetrabromide and triphenylphosphine.

Compounds of formula ArOH can also be prepared by standard functional group transformations well known in the art of organic chemistry, for example, from the corresponding nitroaryl (ArNO$_2$), aniline (ArNH$_2$), or methoxyaryl (ArOMe) precursors. For instance compounds of formula ArOH (IV) can be prepared via diazotisation of the corresponding aniline (III) using sodium nitrite and conc. sulphuric acid as shown in Scheme 1

Scheme 1

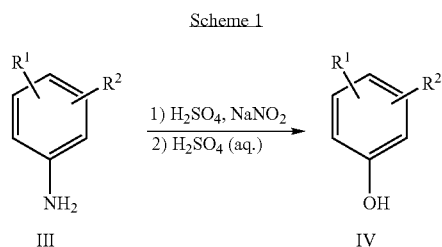

A further route to compounds of formula ArOH (IV) is via demethylation of the corresponding methoxyaryl derivative (V) with pyridine hydrochloride as shown in Scheme 2.

Scheme 2

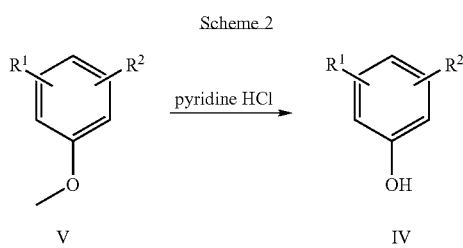

When Ar is benzo[b]thiophene, compounds of formula ArOH can be prepared by literature procedures or modifications of literature procedures known to persons skilled in the art, for example, the procedures disclosed in WO 04/043904. A preferred route to benzo[b]thiophenes is by the alkylation of a thiophenol derivative (VI) with bromoacetaldehyde diethyl acetal (VII) followed by acid catalysed deprotection and subsequent cyclisation with boron trifluoride etherate (Scheme 3). Demethylation of the methoxythiophene (X) provides the hydroxybenzo[b]thiophene (XI) needed for subsequent ether formation.

Scheme 3

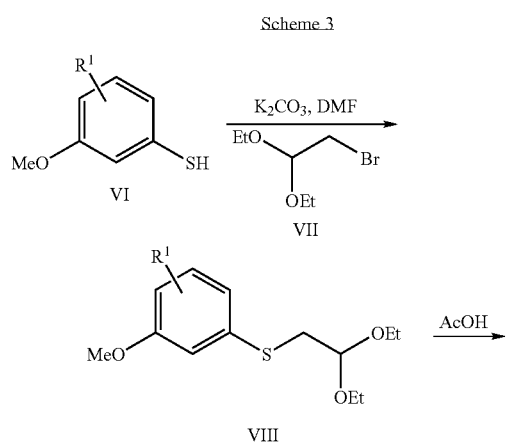

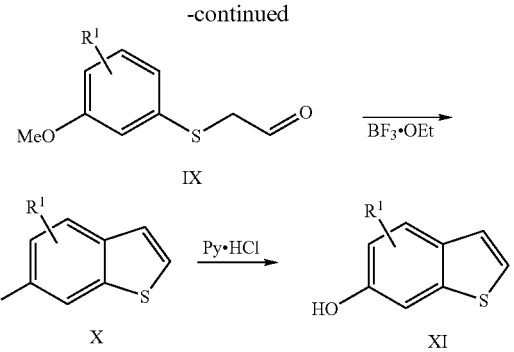

When Ar is benzo[d]isothiazole, compounds of formula ArOH can be prepared by literature procedures or modifications of literature procedures known to persons skilled in the art, for example, utilising procedures disclosed in WO 04/043904. A preferred route to 3-hydroxybenzo[d]isothiazoles is shown in Scheme 4. Treatment of the fluorobenzoic acid (XII) with, for example, oxalyl chloride or thionyl chloride, followed by treatment with ammonia provides the benzamide (XIII). Substitution with benzyl mercaptan then affords the adduct (XIV) which following subsequent cyclisation is converted to the 3-hydroxybenzo[d]isothiazole derivative (XV) needed for subsequent ether formation.

Scheme 4

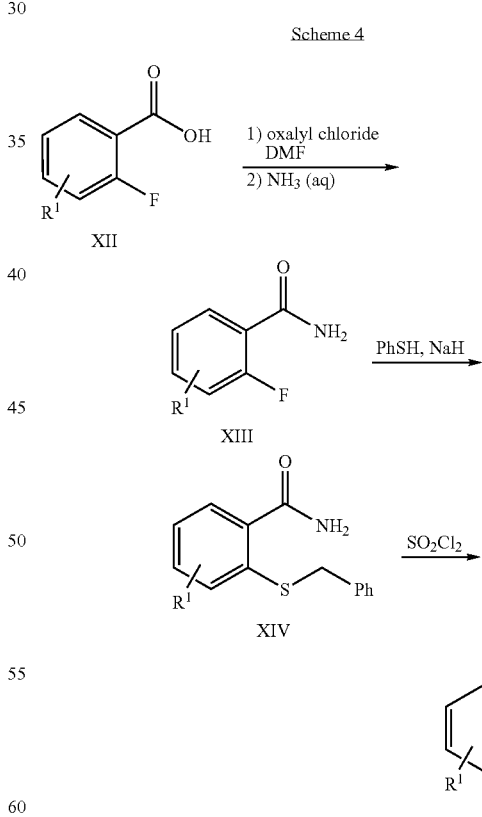

When Ar is benzo[b]furan, compounds of formula ArOH can be prepared by literature procedures or modifications of literature procedures known to persons skilled in the art, see, for example, *SYNLETT*, 1997, 1163. A preferred route to benzo[b]furans is by the reaction of o-triisopropylsiloxyaryl aldehyde derivatives (XVI) with the lithium salt of trimethylsilyldiazomethane followed by conversion to the benzo[b]furan derivative (XVIII) by treatment of the intermediate silyl ether (XVII) with tetra-n-butylammonium fluoride. Subsequent demethylation provides the hydroxybenzo[b]furans (XIX) needed for subsequent ether formation (Scheme 5).

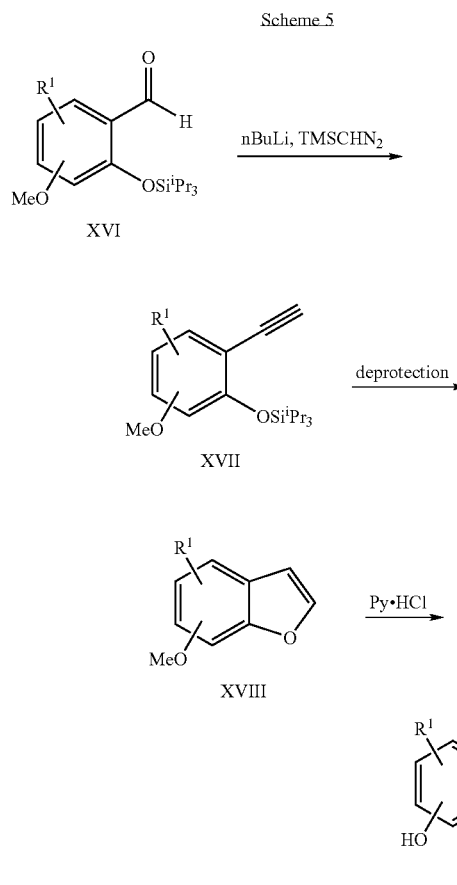

When Ar is pyridyl, compounds of formula ArOH can be prepared by literature procedures or modifications of literature procedures known to persons skilled in the art. For example, halo substituted pyridyls can be prepared via methylation of hydroxypyridyl derivative (XX) followed by reduction of the nitropyridyl derivative (XXI) with, for example, tin chloride to furnish the aniline (XXII). Upon diazotisation and chlorination the pyridine (XXIII) is obtained. Subsequent demethylation provides the hydroxypyridyls (XXIV) needed for subsequent ether formation (Scheme 6).

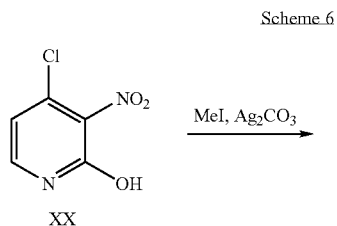

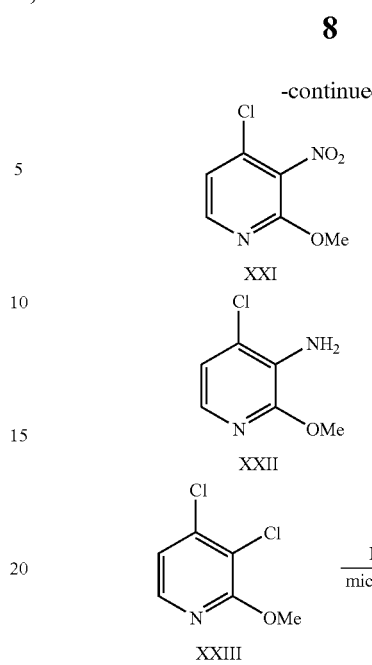

When Ar is naphthyl, compounds of formula ArOH can be prepared by literature procedures or modifications of literature procedures known to persons skilled in the art, see for example *J. Org. Chem.*, 1991, 56(23), 6704 and *J. Org. Chem.*, 1995, 56(23), 6704. For example hydroxynaphthyls can be prepared by bromination of tetralone derivatives (XXV) using bromine and catalytic hydrochloric acid. Subsequent dehydrobromination of the bromide (XXVI) with lithium bromide and lithium carbonate affords the naphthol derivative (XXVII) for subsequent ether formation (Scheme 7).

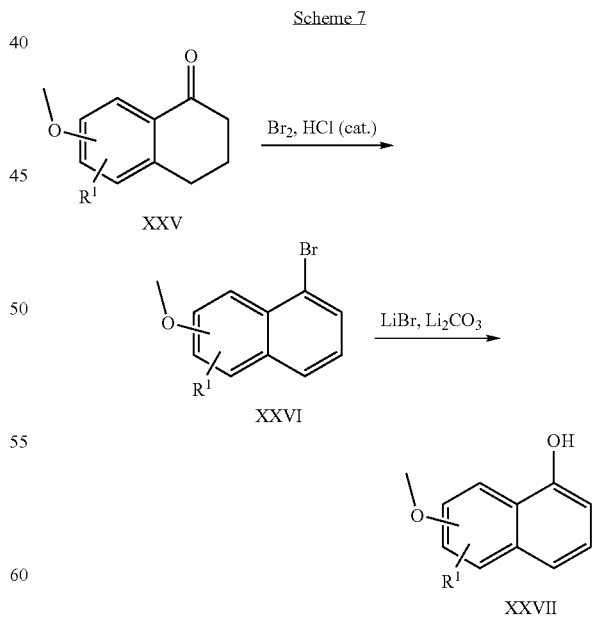

Alternatively the hydroxynaphthyls needed for preparing the compounds of the invention can be obtained via treatment of furan derivatives with isoamyl nitrite and aminobenzoic acid derivatives (XXVIII) to give the cycloadduct (XXIX) via a substituted benzyne intermediate. Treatment with concentrated hydrochloric acid in methanol provides a mixture of 2-substituted naphthol derivatives (XXX) and (XXXI) for subsequent ether formation (Scheme 8).

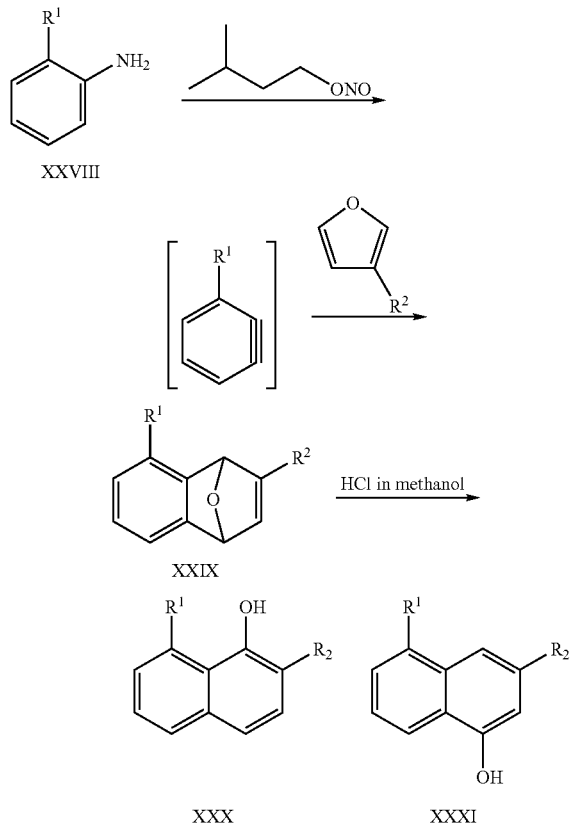

When X is $NR^2$, the 9-azabicyclo[3.3.1]nonane derivatives of Formula I (XXXIV) can be obtained upon treatment of compounds of Formula XXXII, wherein $R^1$ has the meaning as previously defined, with an aniline $ArNH_2$, wherein Ar has the meaning as previously defined, and subsequent reduction of the intermediate imine (XXXIII) with a reducing agent such as $LiAlH_4$ (Scheme 9). The aniline NH can be further derivatised using standard alkylation, acetylation methods well known in the art of organic chemistry, see for example, J. March, 'Advanced Organic Chemistry' 4th Edition, John Wiley and Sons.

Scheme 9

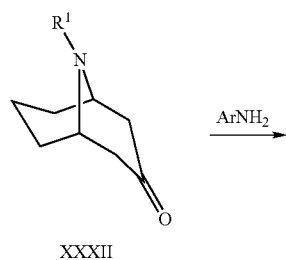

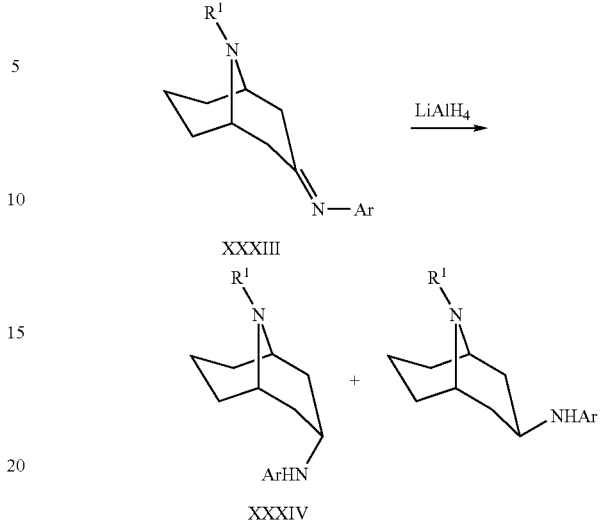

The present invention also includes within its scope all stereoisomeric forms of a 9-azabicyclo[3.3.1]nonane derivative as disclosed herein. In particular, the invention includes both exo and endo stereoisomers resulting when the 3-substituent is in the exo and endo configuration respectively. In the case of individual stereoisomers of compounds of formula I or salts or solvates thereof, the present invention includes the aforementioned stereoisomer substantially free, i.e., associated with less than 5%, preferably less than 2% and in particular less than 1% of the other stereoisomer. Mixtures of stereoisomers in any proportions are also included within the scope of the present invention.

The present invention also includes within its scope all isotopically labelled forms of the compounds of the invention. For example, compounds isotopically labelled with $^2H$, $^3H$, $^{11}C$, $^{13}C$, $^{14}C$, $^{131}I$, $^{125}I$, $^{123}I$ and $^{18}F$. The labelled compounds are useful as diagnostic tools, radio tracers, or monitoring agents in various diagnostic methods and for in vivo receptor imaging.

The 9-azabicyclo[3.3.1]nonane derivatives of the present invention, in the form as a free base, are isolated from reaction mixtures as pharmaceutically acceptable salts. These salts are also obtained by treatment of said free base with an organic or inorganic acid such as hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid. All salts, whether pharmaceutically acceptable or not are included within the scope of the present invention.

The 9-azabicyclo[3.3.1]nonane derivatives of the present invention exist in both solvated and unsolvated forms, including hydrated forms. Both these forms are encompassed within the scope of the present invention.

The 9-azabicyclo[3.3.1]nonane derivatives of the present invention also exist as amorphous forms. Multiple crystalline forms are also possible. All these physical forms are included within the scope of the present invention.

The 9-azabicyclo[3.3.1]nonane derivatives of the present invention are, inter alia, mixed neurotransmitter reuptake inhibitors as demonstrated in vitro by their ability to inhibit the reuptake of one or more of serotonin, noradrenaline and dopamine in cells stably transfected with, for example, the human serotonin, noradrenaline and dopamine transporters. Consequently, the 9-azabicyclo[3.3.1]nonane derivatives of the present invention are useful in therapy. As such, the 9-azabicyclo[3.3.1]nonane derivatives of the present invention are useful in the manufacture of a medicament for the treatment or prevention of diseases for which the reuptake inhibition of one or more monoamine neurotransmitters contributes to the therapeutic effect. In particular, the 8-azabicyclo[3.2.1]octane derivatives of the present invention are useful for the manufacture of a medicament for the treatment or prevention of diseases of the nervous system, both centrally and peripherally, for which the reuptake inhibition of one or more monoamine neurotransmitters contributes to the therapeutic effect.

In a further aspect the 9-azabicyclo[3.3.1]nonane derivatives of the present invention are useful for the treatment or prevention of depression, anxiety, pain, panic disorders and obsessive compulsive disorder. Depression states in the treatment of which the 8-azabicyclo[3.2.1]octane derivatives of the present invention and their pharmaceutically acceptable salts and solvates are particularly useful are those classified as mood disorders in the *Diagnostic and Statistical Manual of Mental Disorders, Fourth Edition—Text Revised*, American Psychiatric Association, Washington D.C. (2000), including mood episodes, depressive disorders, bipolar disorders and other mood disorders.

The present invention further includes a method for the treatment of a mammal, including a human, suffering from or liable to suffer from any of the aforementioned diseases or disorders, said method comprising administering an effective amount of a 9-azabicyclo[3.3.1]nonane derivative of the present invention or a pharmaceutically acceptable salt or solvate thereof.

The amount of a 9-azabicyclo[3.3.1]nonane derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is usual to present it as a pharmaceutical formulation. The present invention therefore also provides a pharmaceutical composition comprising a 9-azabicyclo[3.3.1]nonane derivative according to the present invention in admixture with one or more pharmaceutically acceptable excipients, such as the ones described in Gennaro et. al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a 9-azabicyclo[3.3.1]nonane derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The 9-azabicyclo[3.3.1]nonane derivatives of the present invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The following Examples further illustrate the compounds of the present invention and methods for their synthesis.

In the following section, there is described the synthesis of precursors and common intermediates for compounds of the present invention.

endo-3-Hydroxy-9-azabicyclo[3.3.1]nonane-9-carboxylic acid tert-butyl ester a) 9-Benzyl-9-azabicyclo[3.3.1]nonan-3-one

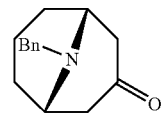

Glutaraldehyde (25% solution in water) (910 mL, 2.4 mol) and benzylamine hydrochloride (344.1 g, 2.4 mol) in water (1050 mL) was cooled to 0° C. 3-Oxopentanedioic acid (350.0 g, 2.4 mol) was added followed by addition of sodium acetate (aq.) (79.7 g in 797 mL water) resulting in formation of a thick orange precipitate. The reaction mixture was heated to 50° C. and stirred at this temperature for 4 h. It was then cooled to ambient temperature and allowed to stand for 24 h. The reaction mixture was acidified to pH2 with 5N aqueous hydrochloric acid (~150 mL) and the resulting aqueous mixture was washed with diethyl ether (2×500 mL). The aqueous extracts were basified to pH12 with 4N aqueous sodium hydroxide (~650 mL) and extracted with dichloromethane (6×500 mL). The organic phase was dried (MgSO$_4$) and concentrated under reduced pressure to afford the crude product as a red oil. Purification by chromatography on silica gel with dichloromethane:methanol (49:1, v/v) as eluent afforded 9-benzyl-9-azabicyclo[3.3.1]nonan-3-one (300.0 g, 1.3 mol, 54%) as a pale orange solid.

b) endo-9-Benzyl-9-azabicyclo[3.3.1]nonan-3-ol

Sodium borohydride (6.22 g, 0.16 mol) was added portionwise (30 min) to a solution of 9-benzyl-9-azabicyclo[3.3.1]nonan-3-one (25.00 g, 0.11 mol) in methanol (130 mL)

cooled to 0° C. under a nitrogen atmosphere. The reaction mixture was warmed to ambient temperature and stirring continued at this temperature for 12 h. The reaction mixture was quenched with acetone (10 mL) and volatiles evaporated in vacuo. The resultant yellow solid was dissolved in water (110 mL) and extracted with dichloromethane (3×40 mL). The organic phase was dried (MgSO$_4$) and evaporated under reduced pressure to afford crude endo-9-benzyl-9-azabicyclo[3.3.1]nonan-3-ol (25.25 g, 0.11 mol, 100%) as a yellow solid.

c) endo-9-Azabicyclo[3.3.1]nonan-3-ol

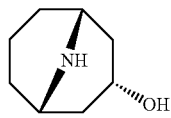

10% Palladium on carbon (10% Pd/C) (5.0 g) was added to a solution of endo-9-benzyl-9-azabicyclo[3.3.1]nonan-3-ol (27.0 g, 0.12 mol) in ethanol (500 mL) and 5N aqueous hydrochloric acid (25 mL). The mixture was stirred under a hydrogen atmosphere (3 bar) at 40° C. for 48 h.

The mixture was then filtered through a pad of dicalite and the filtrate was evaporated in vacuo and remaining aqueous mixture azeotroped with toluene (2×150 mL) to yield crude endo-9-azabicyclo[3.3.1]nonan-3-ol as a pale yellow solid which was used directly in the next stage.

d) endo-3-Hydroxy-9-azabicyclo[3.3.1]nonane-9-carboxylic acid tert-butyl ester

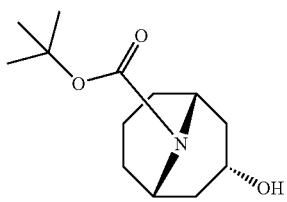

Crude endo-9-azabicyclo[3.3.1]nonan-3-ol (from Step c) was dissolved in a solution of dioxane (500 mL), water (187.5 mL) and 4N sodium hydroxide (aq.) (62.5 mL) and cooled to −15° C. under a nitrogen atmosphere. Di-tert-butyl dicarbonate (39.0 g, 0.18 mol) was added portionwise over 10 min, the reaction mixture allowed to warm to ambient temperature and stirring continued for 4 h during which time a white precipitate formed. Dioxane was evaporated under reduced pressure. Water (400 mL) was added and the product extracted with dichloromethane (3×400 mL). The organic phase was dried (MgSO$_4$) and concentrated in vacuo to afford endo-3-hydroxy-9-azabicyclo[3.3.1]nonane-9-carboxylic acid tert-butyl ester (24.0 g, 0.10 mol, 83% from endo-9-benzyl-9-azabicyclo[3.3.1]nonan-3-ol) as a pale yellow solid.

exo-3-Hydroxy-9-azabicyclo[3.3.1]nonane-9-carboxylic acid tert-butyl ester a) exo-9-Benzyl-9-azabicyclo[3.3.1]nonan-3-ol

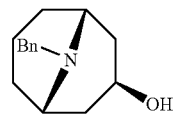

Sodium (1.6 g, 69.8 mmol) was added portionwise to a solution of 9-benzyl-9-azabicyclo[3.3.1]nonan-3-one (1.0 g, 4.36 mmol) in 1-pentanol (50 mL) heated at reflux temperature. The reaction mixture was heated at 136° C. for 2 h followed by cooling to ambient temperature. 5N aqueous HCl (50 mL) was added, the aqueous layer separated and the organic phase extracted with further 5N aqueous HCl (5×50 mL). The aqueous extracts were washed with diethyl ether (3×70 mL) and basified by addition of 10N aqueous KOH (taken to pH8) followed by saturated aqueous K$_2$CO$_3$. The aqueous mixture was extracted with dichloromethane (5×40 mL) and the organic phase washed with brine (60 mL), dried (Na$_2$SO$_4$) and concentrated in vacuo to afford exo-9-benzyl-9-azabicyclo[3.3.1]nonan-3-ol (1.93 g, 96%) as a brown oil.

Data for exo-9-benzyl-9-azabicyclo[3.3.1]nonan-3-ol:: MS (ESI) m/z: 232 ([M+H]+).

b) exo-9-Azabicyclo[3.3.1]nonan-3-ol

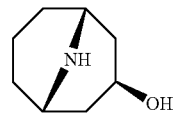

The procedure for the preparation of endo-9-azabicyclo[3.3.1]nonan-3-ol was followed to afford exo-9-azabicyclo[3.3.1]nonan-3-ol (5.0 g, 100%) as a pale yellow oil.

Data for exo-9-azabicyclo[3.3.1]nonan-3-ol:: MS (ESI) m/z: 142 ([M+H]+).

c) exo-3-Hydroxy-9-azabicyclo[3.3.1]nonane-9-carboxylic acid tert-butyl ester

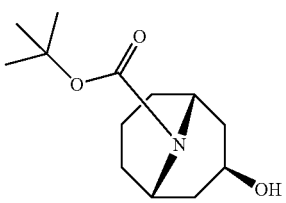

The procedure for the preparation of endo-3-hydroxy-9-azabicyclo[3.3.1]nonane-9-carboxylic acid tert-butyl ester was followed to afford exo-3-hydroxy-9-azabicyclo[3.3.1]nonane-9-carboxylic acid tert-butyl ester (663 mg, 71%) as a pale yellow oil.

Benzo[d]isothiazol-6-ol a) 6-Methoxybenzo[d]isothiazole

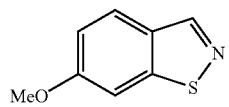

A method similar to that described for the synthesis of 7-methoxybenzo[d]isothiazole in WO 04/043904 was used from 2-fluoro-4-methoxybenzaldehyde (1 g, 6.49 mmol), sulphur (208 mg, 6.49 mmol), 2-methoxyethanol (10 mL) and aqueous ammonia (30%, 10 mL). The product was collected as a pale yellow oil (650 mg, 61%).

Data for 6-methoxybenzo[d]isothiazole: MS (ESI) m/z: 166 ([M+H]+).

b) Benzo[d]isothiazol-6-ol

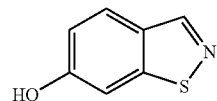

A method similar to the method described in WO 04/043904 was used. 6-Methoxybenzo[d]isothiazole (450 mg, 2.73 mmol) and pyridine hydrochloride (3.2 g, 27.27 mmol) were heated at 210° C. in a microwave oven for 20 min. The residue was partitioned between water (30 mL) and EtOAc (3×20 mL). The combined organic layers were dried (MgSO$_4$) and concentrated in vacuo. The residue was purified by chromatography on silica gel with EtOAc:heptane (1:1, v/v) as eluent to afford benzo[d]isothiazol-6-ol as a white solid (345 mg, 83%).

Data for benzo[d]isothiazol-6-ol: MS (ESI) m/z: 152 ([M+H]$^+$).

Benzo[d]isothiazol-5-ol a) 5-Nitrobenzo[d]isothiazole

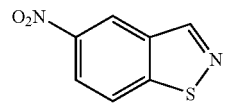

2-Chloro-5-nitrobenzaldehyde (1 g, 5.39 mmol) was added to a mixture of aqueous ammonia (30%, 3.3 mL) and DMF (3.3 mL) and sulphur (181 mg, 5.66 mmol) was added. The suspension was heated to 90° C. over 30 min and the resultant dark solution maintained at this temperature for 1 h. The mixture was cooled to ambient temperature, diluted with water and poured over ice. An orange solid was filtered off, washed with water and dried under suction to afford 5-nitrobenzo[d]isothiazole (861 mg, 89%).

b) 5-Aminobenzo[d]isothiazole

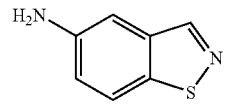

5-Nitrobenzo[d]isothiazole (305 mg, 1.69 mmol), 5% AcOH (aq.) (12 mL) and EtOAc (12 mL) at 65° C. was treated with iron powder (325 mesh, 473 mg) and stirred rapidly for 1 h. The mixture was cooled to ambient temperature, diluted with water and EtOAc and filtered through dicalite. The organic layer was separated and the aqueous layer extracted with further EtOAc. The combined organic extracts were washed with brine, dried (MgSO$_4$) and concentrated in vacuo to give the title compound as a yellow solid (220 mg, 85%).

Data for 5-aminobenzo[d]isothiazole: MS (ESI) m/z: 151 ([M+H]+).

c) Benzo[d]isothiazol-5-ol

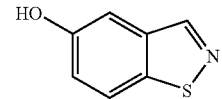

5-Aminobenzo[d]isothiazole (217 mg, 1.45 mmol) was suspended/dissolved in water (20 mL) containing concentrated sulphuric acid (1.5 mL) and heated at 90° C. for 2 h. This solution was cooled to 0° C. and sodium nitrite (105 mg, 1.52 mmol) in water (1 mL) was added over 5 min and the mixture allowed to warm to ambient temperature. The diazonium salt was added dropwise over 20 min to a solution of concentrated sulphuric acid (1 mL) in water (12 mL) at 90° C. and stirred at this temperature for 2 h before hot filtering to remove an insoluble solid. The filtrate was extracted with dichloromethane (3×20 mL) and the combined organic extracts washed with brine (50 mL), dried (MgSO$_4$) and concentrated in vacuo to give the title compound as a brown solid (65 mg, 30%).

Data for benzo[d]isothiazol-5-ol: MS (ESI) m/z: 152 ([M+H]+).

5-Chlorobenzo[d]isothiazol-3-ol a) 5-Chloro-2-fluorobenzamide

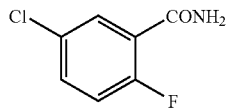

5-Chloro-2-fluorobenzoic acid (1 g, 5.73 mmol) was suspended in dichloromethane (10 mL) and DMF (1 drop) was added followed by dropwise addition of oxalyl chloride (0.75 mL, 8.59 mmol). The mixture was stirred at ambient temperature for 1 h by which time gas evolution had ceased and a colourless solution resulted. This acid chloride was concentrated in vacuo, dissolved in dichloromethane (10 mL) and added dropwise to aqueous ammonia (30%, 40 mL). This mixture was stirred for a further 30 min and then extracted with dichloromethane (3×20 mL). The combined extracts were dried (MgSO$_4$) and concentrated in vacuo resulting in a white solid (900 mg, 91%).

b) 2-Benzylsulphanyl-5-chlorobenzamide

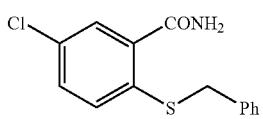

Benzyl mercaptan (0.61 mL, 5.20 mmol) was added dropwise over 10 min to a stirred suspension of sodium hydride (60% in oil, 230 mg, 5.75 mmol) in THF (10 mL) at ambient temperature under a nitrogen atmosphere. The white suspension was stirred for a further 1 h and then added dropwise to a stirred solution of 5-chloro-2-fluorobenzamide (900 mg, 5.20 mmol) in THF (10 mL), under nitrogen, over 10 min. The mixture was stirred at ambient temperature for 1 h, at 50° C. for 1 h and at reflux for 3 h and then quenched with water (200 mL). The product mixture was extracted with EtOAc (3×30 mL) and the combined extracts washed with brine (50 mL), dried (MgSO$_4$) and concentrated in vacuo. The crude product was purified by chromatography on silica gel with EtOAc: heptane (3:2, v/v) as eluent to give the title compound as a white solid (523 mg, 36%).

c) 5-Chlorobenzo[d]isothiazol-3-ol

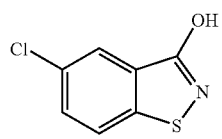

2-Benzylsulphanyl-5-chlorobenzamide (523 mg, 1.89 mmol) was dissolved in dichloromethane (20 mL) and sulphuryl chloride (0.183 mL, 3.29 mmol) added dropwise. The resultant white suspension was stirred for a further 1 h, diluted with heptane (15 mL), filtered, washed with heptane and dried under suction to afford the title compound as a white solid (413 mg, >100%).

Data for 5-chlorobenzo[d]isothiazol-3-ol: MS (ESI) m/z: 186.1 ([M+H]+).

7-Fluorobenzo[d]isothiazol-4-ol a) 7-Fluoro-4-methoxnbenzo[d]isothiazole

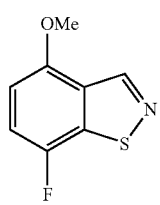

A method similar to that described for the synthesis of 7-methoxybenzo[d]isothiazole in WO 04/043904 was used from 2,3-difluoro-6-methoxybenzaldehyde (prepared as described in WO 04/043904) (2.0 g, 11.62 mmol), sulphur (372 mg, 11.62 mmol), 2-methoxyethanol (10 mL) and aqueous ammonia (30%, 10 mL). The product was isolated as a pale yellow oil (2.0 g, 94%).

b) 7-Fluorobenzo[d]isothiazol-4-ol

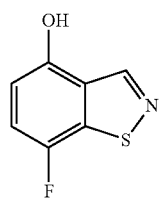

A method similar to that described for the synthesis of benzo[d]isothiazol-7-ol in WO 04/043904 was used from 7-fluoro-4-methoxybenzo[d]isothiazole (500 mg, 27.32 mmol) and pyridine hydrochloride (2.5 g, 21.74 mmol) to give the title compound as grey solid (420 mg, 65%).

Data for 7-fluorobenzo[d]isothiazol-4-ol: MS (ESI) m/z: 170 ([M+H]$^+$).

6-Chlorobenzo[d]isothiazol-3-ol a) 4-Chloro-2-fluorobenzamide

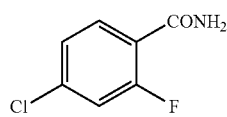

A method similar to the preparation of 5-chloro-2-fluorobenzamide (see page 17 above) was followed using 4-chloro-2-fluorobenzoic acid (500 mg, 5.73 mmol). The title compound was isolated as an off-white solid (465 mg, 94%).

Data for 4-chloro-2-fluorobenzamide: MS (ESI) m/z: 174 ([M+H]$^+$).

b) 2-benzylsulphanyl-4-chlorobenzamide

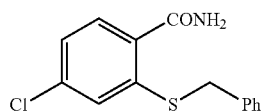

A method similar to the preparation of 2-benzylsulphanyl-5-chlorobenzamide (see page 17 above) was followed using 4-chloro-2-fluorobenzamide (400 mg, 2.31 mmol). The title compound was isolated as a white solid (376 mg, 59%).

Data for 2-benzylsulphanyl-4-chlorobenzamide: MS (ESI) m/z: 278 ([M+H]$^+$).

c) 6-Chlorobenzo[d]isothiazol-3-ol

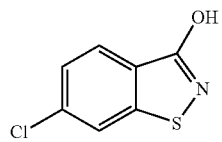

A method similar to the preparation of 5-chlorobenzo[d]isothiazol-3-ol (see pages 17 and 18 above) was followed using 2-benzylsulphanyl-4-chlorobenzamide (350 mg, 1.26 mmol). The title compound was isolated as a white solid (150 mg, 64%).

Data for 6-chlorobenzo[d]isothiazol-3-ol: MS (ESI) m/z: 186/188 ([M+H]$^+$).

Benzo[b]thiophene-6-ol a) 1-(2,2-Diethoxyethylsulphanyl)-3-methoxybenzene

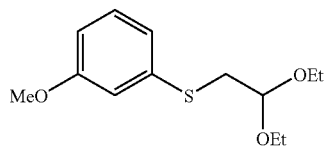

3-Methoxythiophenol (10.00 g, 71.33 mmol), bromoacetaldehyde diethyl acetal (11.47 mL, 76.24 mmol), potassium carbonate (10.35 g, 74.89 mmol) and acetone (100 mL) were stirred at ambient temperature under nitrogen for 3 h. The white suspension was filtered, washed with acetone (2×25 mL) and the combined filtrate and washings concentrated to dryness in vacuo. The residue was dissolved in ethyl acetate (50 mL) and washed with 0.5N NaOH (aq.) (2×15 mL), water 15 mL) and brine (15 mL). The organic layer was dried (MgSO$_4$) and concentrated in vacuo and then further dried at 130° C. under high vacuum to give the title compound (18.74 g, quantitative).

b) (3-Methoxyphenylsulphanyl)acetaldehyde

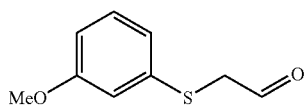

1-(2,2-Diethoxyethylsulphanyl)-3-methoxybenzene (18 g, 70.21 mmol), glacial acetic acid (26 mL) and water (18 mL) were stirred at reflux temperature under nitrogen for 45 min. The reaction mixture was cooled to ambient temperature, diluted with water (180 mL) and extracted with tert-butyl methyl ether (3×40 mL). The combined extracts were cooled to <5° C. and washed with 5% aqueous sodium carbonate solution, water, and brine. The organic phase was dried (MgSO$_4$) and concentrated in vacuo to yield the title compound (11.8 g, 92%).

c) 6-Methoxybenzo[b]thiophene

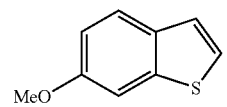

Boron trifluoride etherate (8.15 mL) dissolved in dry dichloromethane (407 mL) was stirred rapidly at 0° C. under nitrogen and a solution of (3-methoxyphenylsulphanyl)acetaldehyde (11.5 g, 63.10 mmol) in dry dichloromethane (29 mL) was added dropwise over 25 min. The resultant green solution was stirred for 2 min and then saturated aqueous sodium bicarbonate solution (150 mL) was added at a rate so as to maintain the temperature <8° C. The reaction mixture was stirred for 5 min and then the layers were separated and the organic layer was washed with saturated aqueous sodium bicarbonate solution (100 mL) and water (100 mL). The organic phase was dried (MgSO$_4$), and concentrated in vacuo. The product was purified by distillation to afford the title compound as a colourless oil (6.29 g, 61%, b.p. 83-88° C. at 16 mBar).

d) Benzo[b]thiophen-6-ol

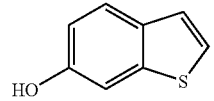

6-Methoxybenzo[b]thiophene (6.15 g, 37.45 mmol) and pyridine hydrochloride (18.5 g) were heated together at 210° C. for 1 h. The mixture was cooled to 100° C., diluted with water (125 mL) and extracted with dichloromethane (3×70 mL). The combined extracts were washed with water (125 mL), dried (MgSO$_4$) and evaporated in vacuo to give the title compound (5.54 g, 98%)

4-Chlorobenzo[b]thiophen-7-ol

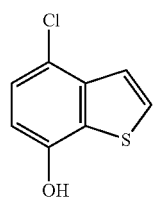

4-Bromo-7-methoxybenzo[b]thiophene (prepared as described in *J. Chem. Soc. (Perkin Trans I)*, 1983, 2973-2977) (1.2 g, 4.96 mmol) and pyridine hydrochloride (1.95 g, 16.87 mmol) was heated at 210° C. in a microwave for 15 min. The mixture was partitioned between HCl (aq.) (20 mL) and EtOAc (20 mL). The aqueous phase was washed with additional EtOAc (3×20 mL) and the organic phase was dried (Na$_2$SO$_4$) and concentrated in vacuo. The product was purified by chromatography on silica gel with EtOAc:heptane (1:10 to 1:5, v/v) as eluent to give the title compound as a red oil (372 mg, 41%).

Data for 4-chlorobenzo[b]thiophen-7-ol: MS (ESI) m/z: 185/187 ([M+H]+).

3,5-Dibromophenol

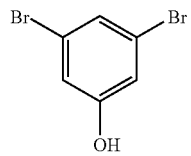

Pentabromophenol (1.0 g, 2.05 mmol) and AlCl$_3$ (4.1 g, 30.75 mmol) were mixed in toluene (20 mL) and heated at reflux temperature under a nitrogen atmosphere overnight. The reaction mixture was cooled, cautiously added to ice, filtered and the filtrate was extracted with EtOAc (3×50 mL). The organics were dried (Na$_2$SO$_4$) and concentrated in vacuo. The residue obtained was purified by chromatography on silica gel with EtOAc:heptane (1:4, v/v) as eluent to afford the title compound as a white solid (230 mg, 0.91 mmol, 45%).

3,4-Dichloro-2-fluorophenol

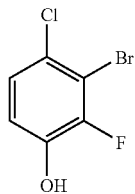

Trifluoroacetic acid (0.5 mL) was added to a solution of 3-chloro-2-fluorophenol (750 mg, 5.12 mmol) and N-chlorosuccinimide (684 mg, 5.12 mmol) in acetonitrile (30 mL) and the reaction mixture stirred for 24 h. The mixture was concentrated in vacuo and purified by chromatography on silica gel with heptane:EtOAc (9:1, v/v) as eluent to afford the title compound (440 mg, 48%) as a pale yellow solid.

2,3-Dichloro-4-fluoroPhenol

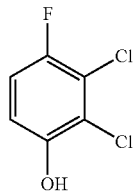

3-Chloro-4-fluorophenol (500 mg, 3.4 mmol) was dissolved in acetonitrile (25 mL) and trifluoroacetic acid (500 mL) was added, followed by addition of N-chlorosuccinimide (456 mg, 3.4 mmol). The reaction was stirred at ambient temperature for 3 days and the volatiles were then removed in vacuo. The crude product was purified by chromatography on silica gel with EtOAc:isohexane (1:19, v/v) as eluent to afford of 3,6-dichloro-4-fluorophenol (261 mg, 1.4 mmol, 42%) and 2,3-dichloro-4-fluorophenol (153 mg, 0.8 mmol, 25%).

3-Chloro-2-methylphenol

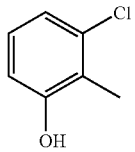

A solution of concentrated sulphuric acid (7.3 mL) in water (97 mL) was added to 3-chloro-2-methylaniline (0.84 mL, 7.06 mmol) and the mixture heated at 90° C. until solution was achieved. The reaction mixture was cooled to 0° C. and a solution of sodium nitrite (510 mg, 12.75 mmol) in water (5 mL) was added dropwise. The reaction mixture was allowed to warm to ambient temperature over 2 h. Excess sodium nitrite was destroyed by the addition of urea. The resultant mixture was added to a solution of concentrated sulphuric acid (5.0 mL) in water (55 mL), heated to 90° C. and stirred at this temperature for a further 1 h. The resultant product mixture was filtered through dicalite and extracted with dichloromethane (2×200 mL). The organic phase was washed with NaHCO$_3$ (aq.), dried (MgSO$_4$) and evaporated under reduced pressure to afford the desired product (830 mg, 83%) as an off-white solid.

Similarly prepared were:
3-Fluoro-2-methylphenol
3-Methyl-5-trifluoromethylphenol
3-Chloro-4-trifluoromethylphenol
4-Chloro-3-trifluoromethylphenol
2-Methyl-3-trifluoromethylphenol
3-Bromo-4-methylphenol 3,4-Dichloro-2-hydroxypyridine a) 4-Chloro-2-methoxy-3-nitropyridine

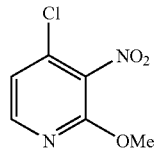

Methyl iodide (2.06 mL, 32.99 mmol) was added to a suspension of 4-chloro-2-hydroxy-3-nitropyridine (prepared as described in *Bioorg. Med. Chem. Lett.*, 2003, 13, 125) (2.87 g, 16.49 mmol) and silver carbonate (4.55 g, 16.49 mmol) in toluene (100 mL) and the mixture heated at 85° C. for 3.5 h. On cooling to ambient temperature the mixture was filtered through dicalite and washed with toluene. The combined filtrate and washings were concentrated in vacuo and the crude product purified by chromatography on silica gel with EtOAc:heptane (1:9, v/v) as eluent. The pure product was collected as a white solid (1.99 g, 64%).

Data for 4-chloro-2-hydroxy-3-nitropyridine: MS (ESI) m/z:189/191 ([M+H]+).

b) 3-Amino-4-chloro-2-methoxypyridine

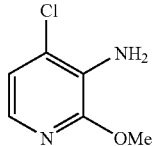

Tin(II)chloride dihydrate (12 g, 53.19 mmol) was added to a solution of 4-chloro-2-methoxy-3-nitropyridine (2 g, 10.64 mmol) in ethyl acetate (30 mL) and the resultant suspension heated at 70° C. with stirring for 2 h. The reaction mixture was cooled to ambient temperature, the pH adjusted to pH 9-10 by addition of saturated sodium carbonate (aq.) and extracted with ethyl acetate (3×100 mL). The combined extracts were dried (MgSO$_4$) and concentrated in vacuo to give the crude product. Purification by chromatography on silica gel with EtOAc:heptane (1:9, v/v) as eluent afforded the product as a colourless oil (1.28 g, 76%).

Data for 3-amino-4-chloro-2-methoxypyridine: MS (ESI) m/z:159/161 ([M+H]+).

c) 3,4-Dichloro-2-methoxypyridine

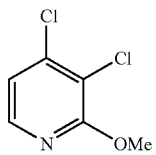

3-Amino-4-chloro-2-methoxypyridine (200 mg, 1.27 mmol), dissolved in conc. hydrochloric acid (4 mL) was stirred at −5° C. while a solution of sodium nitrite (437 mg, 6.33 mmol) in water (2 mL) was added dropwise over 10 min. The mixture was stirred for a further 10 min before copper chloride (1.25 g, 12.66 mmol) was added portionwise over 5 min. The dark effervescing mixture was stirred at −5° C. for 20 min and then the cooling bath was removed and the mixture stirred at ambient temperature for 1 h. The resultant green solution was basified by addition of 5N sodium hydroxide (aq.), diluted with water (100 mL) and extracted with diethyl ether (3×30 mL). The combined extracts were washed with brine (50 mL), dried (MgSO$_4$) and concentrated in vacuo to yield the title compound (218 mg, 97%).

Data for 3,4-dichloro-2-methoxypyridine: MS (ESI) m/z: 178/180 ([M+H]+).

d) 3,4-Dichloro-2-hydroxypyridine

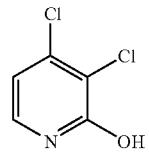

3,4-Dichloro-2-methoxypyridine (192 mg, 1.08 mmol) and 25% aqueous hydrochloric acid (7 mL) was heated at 150° C. in a microwave oven for 5 min and concentrated to dryness in vacuo to afford the product as a pale yellow solid (153 mg, 87%).

Data for 3,4-dichloro-2-hydroxypyridine: MS (ESI) m/z: 164/166 ([M+H]+).

2,3-Dichloro-6-hydroxypyridine a) 3-Amino-2-chloro-6-methoxypyridine

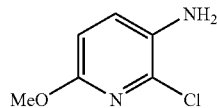

Tin(II)chloride dihydrate (6 g, 26.52 mmol) was added to a solution of 2-chloro-6-methoxy-3-nitropyridine (1 g, 5.30 mmol) in ethyl acetate (15 mL) and the resultant suspension heated at 70° C. with stirring for 1 h. The reaction mixture was cooled to ambient temperature, the pH adjusted to pH 9-10 by addition of saturated sodium carbonate (aq.) and extracted with ethyl acetate (3×50 mL). The combined extracts were dried (MgSO$_4$) and concentrated in vacuo to give the crude product. Purification by chromatography on silica gel with EtOAc:heptane (3:7, v/v) as eluent afforded the product as a pale yellow oil (600 mg, 72%).

Data for 3-amino-2-chloro-6-methoxypyridine: MS (ESI) m/z: 159 ([M+H]+).

b) 2,3-Dichloro-6-methoxypyridine

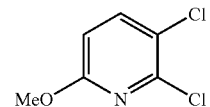

3-Amino-2-chloro-6-methoxypyridine (500 mg, 3.17 mmol) dissolved/suspended in conc. hydrochloric acid (10 mL) was stirred at −5° C. while a solution of sodium nitrite (1.09 g, 15.82 mmol) in water (5 mL) was added dropwise over 10 min. The mixture was stirred for a further 10 min before copper chloride (3.13 g, 31.65 mmol) was added portionwise over 5 min. The dark effervescing mixture was stirred at −5° C. for 20 min and then the cooling bath was removed and the mixture stirred at ambient temperature for 3 h. The mixture was diluted with water (100 mL), basified to pH 10-11 by addition of 5N sodium hydroxide (aq.) and extracted with diethyl ether (3×50 mL). The combined extracts were washed with brine, dried (MgSO₄) and concentrated in vacuo. The crude product was purified by chromatography on silica gel with EtOAc:heptane (1:9, v/v) as eluent to afford the product as a pale yellow oil (229 mg, 41%).

Data for 2,3-dichloro-6-methoxypyridine: MS (ESI) m/z: 178 ([M+H]$^+$).

c) 2,3-Dichloro-6-hydroxypyridine

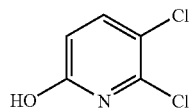

2,3-Dichloro-6-methoxypyridine (211 mg, 1.19 mmol) and 25% hydrochloric acid (aq.) (9 mL) was heated in a microwave oven at 150° C. for 15 min and concentrated to dryness in vacuo to afford the product as a pale green solid (173 mg, 89%).

Data for 2,3-dichloro-6-hydroxypyridine: MS (ESI) m/z: 164/166 ([M+H]$^+$).

2,4-Dichloro-6-hydroxypyridine

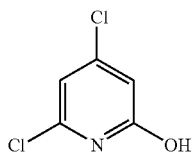

Sodium nitrite (64 mg, 0.93 mmol) dissolved in water (0.6 mL) was added dropwise to a stirred solution of 2-amino-4,6-dichloropyridine (prepared according to the method described in *Recl. Trav. Chim. Pays-Bas,* 1950, 69, 673) (126 mg, 0.77 mmol) in 5% sulphuric acid (5 mL) at 0° C., over 5 min. The mixture was stirred at 0° C. for 1 h and then diluted with water (20 mL) and extracted with dichloromethane (3×20 mL). The combined extracts were washed with brine (20 mL), dried (MgSO₄) and concentrated in vacuo to afford the product as an orange solid (116 mg, 92%).

Data for 2,4-dichloro-6-hydroxypyridine: MS (ESI) m/z: 164/166 ([M+H]$^+$).

The present invention is further illustrated by the following examples:

Procedure I

EXAMPLE I.1 exo-3-(Benzo[d]isothiazol-7-yloxy)-9-azabicyclo[3.3.1]nonane

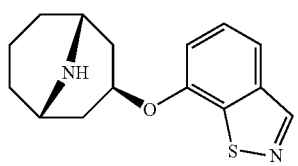

Endo-3-hydroxy-9-azabicyclo[3.3.1]nonane-9-carboxylic acid tert-butyl ester (241 mg, 1.00 mmol), (4,4-dimethyl-1,1-dioxido-1,2,5-thiadiazolidin-2-yl)triphenyl phosphonium (prepared as described in *J. Org. Chem.,* 1994, 59, 2289) (616 mg, 1.50 mmol) and benzo[d]isothiazol-7-ol (prepared as described in WO 04/043904) (151 mg, 1.00 mmol) were dissolved in dry THF (5 mL) in a microwave vial. The reaction was heated at 140° C. for 10 min in the microwave oven. On cooling the solvent was evaporated under reduced pressure. The product was purified by chromatography on silica gel with a gradient of dichloromethane to dichloromethane:methanol (49:1, v/v) to dichloromethane:methanol (19:1, v/v) as eluent to afford crude product (230 mg, 84%). The crude product was dissolved in a solution of trifluroacetic acid (TFA) (1 mL) and dichloromethane (5 mL) and stirred at ambient temperature for 1 h. Volatiles were evaporated under reduced pressure, the residue dissolved in methanol (1 mL) and passed through an SCX cartridge (primed with dilute TFA/methanol), washed with methanol, then product eluted with a solution of 2M ammonia in methanol. The product was further purified by chromatography on slica gel with dichloromethane:methanol (49:1, v/v) to dichloromethane:methanol (19:1, v/v) as eluent to afford exo-3-(benzo[d]isothiazol-7-yloxy)-9-azabicyclo[3.3.1]nonane (90 mg, 53%).

Data for exo-3-(benzo[d]isothiazol-7-yloxy)-9-azabicyclo[3.3.1]nonane: MS (ESI) m/z: 275 ([M+H]$^+$).

Similarly prepared were:

EXAMPLE I.2 exo-3-(Benzo[d]isothiazol-4-yloxy)-9-azabicyclo[3.3.1]nonane

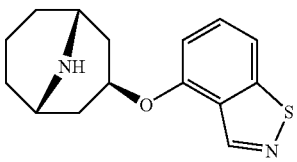

Prepared from benzo[d]isothiazol-4-ol (prepared as described in WO 04/043904). MS (ESI) (m/z): 275 ([M+H]$^+$).

EXAMPLE I.3 exo-3-(Benzo[d]isothiazol-6-yloxy)-9-azabicyclo[3.3.1]nonane

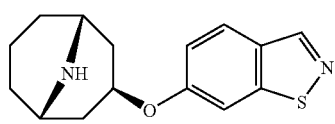

Prepared from benzo[d]isothiazol-6-ol. MS (ESI) (m/z): 275 ([M+H]$^+$).

EXAMPLE I.4 exo-3-(Benzo[d]isothiazol-5-yloxy)-9-azabicyclo[3.3.1]nonane

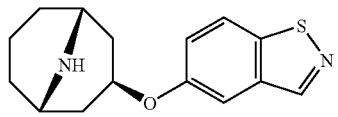

Prepared from benzo[d]isothiazol-5-ol. MS (ESI) (m/z): 275 ([M+H]$^+$).

EXAMPLE I.5 exo-3-(Benzo[d]isothiazol-3-yloxy)-9-azabicyclo[3.3.1]nonane

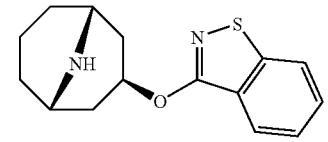

MS (ESI) (m/z): 275 ([M+H]$^+$).

EXAMPLE I.6 exo-3-(7-Fluorobenzo[d]isothiazol-4-yloxy)-9-azabicyclo[3.3.1]nonane

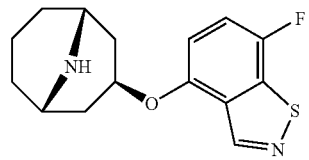

Prepared from 7-fluorobenzo[d]isothiazol-4-ol. MS (ESI) (m/z): 293 ([M+H]$^+$).

EXAMPLE I.7 exo-3-(4-Fluorobenzo[d]isothiazol-7-yloxy)-9-azabicyclo[3.3.1]nonane

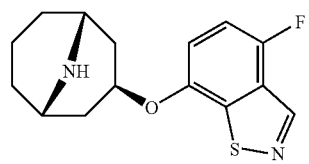

Prepared from 4-fluorobenzo[d]isothiazol-7-ol (prepared by the method described for 7-fluorobenzo[d]isothiazol-4-ol). MS (ESI) (m/z): 293 ([M+H]$^+$).

EXAMPLE I.8 exo-3-(6-Chlorobenzo[d]isothiazol-3-yloxy)-9-azabicyclo[3.3.1]nonane

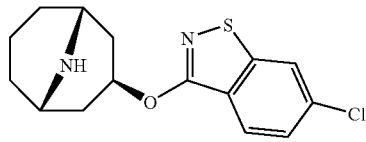

Prepared from 6-chlorobenzo[d]isothiazol-3-ol. MS (ESI) (m/z): 309/311 ([M+H]$^+$).

EXAMPLE I.9 exo-3-(5-Chlorobenzo[d]isothiazol-3-yloxy)-9-azabicyclo[3.3.1]nonane

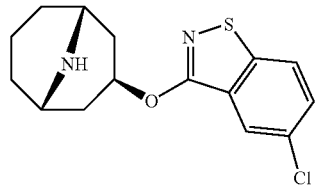

Prepared from 5-chlorobenzo[d]isothiazol-3-ol. MS (ESI) (m/z): 309/311 ([M+H]$^+$).

EXAMPLE I.10 exo-3-(Benzo[d]isoxazol-3-yloxy)-9-azabicyclo[3.3.1]nonane

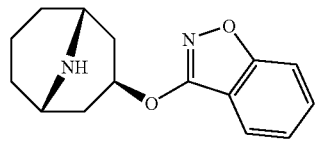

MS (ESI) (m/z): 259 ([M+H]$^+$).

Procedure II

EXAMPLE II.1 exo-3-(3-Chloro-2-fluorophenoxy)-9-azabicyclo[3.3.1]nonane

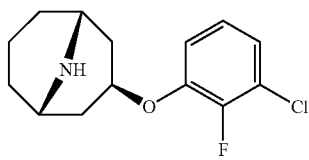

Endo-3-hydroxy-9-azabicyclo[3.3.1]nonane-9-carboxylic acid tert-butyl ester (150 mg, 0.62 mmol), (4,4-dimethyl-1,1-dioxido-1,2,5-thiadiazolidin-2-yl)triphenyl phosphonium (prepared as described in *J. Org. Chem.*, 1994, 59, 2289) (383 mg, 0.93 mmol) and 3-chloro-2-fluorophenol (137 mg, 0.93 mmol) were dissolved in dry THF (4 mL). The reaction mixture was stirred at ambient temperature for 4 h. The solvent was evaporated under reduced pressure, the residue dissolved in dichloromethane (5 mL) and trifluoroacetic acid (2 mL). Stirring was continued for 2 h. Volatiles were evaporated under reduced pressure, the residue dissolved in methanol (1 mL) and passed through an SCX cartridge (primed with dilute TFA/methanol), washed with methanol, then the product was eluted with a solution of 2M ammonia in methanol. The product was further purified by chromatography on silica gel with dichloromethane:methanol:ammonia (aq.) (89.9:10:0.1, v/v) as eluent to afford exo-3-(3-chloro-2-fluorophenoxy)-9-azabicyclo[3.3.1]nonane (45 mg, 27%).

Data for exo-3-(3-chloro-2-fluorophenoxy)-9-azabicyclo[3.3.1]nonane: MS (ESI) m/z:270/272 ([M+H]$^+$).

Similarly prepared were:

EXAMPLE II.2 exo-3-(Indan-4-yloxy)-9-azabicyclo[3.3.1]nonane

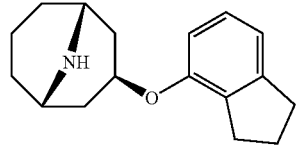

MS (ESI) m/z: 258 ([M+H]$^+$).

EXAMPLE II.3 exo-3-(2,3-Dimethylphenoxy)-9-azabicyclo[3.3.1]nonane

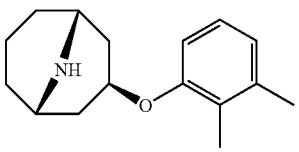

MS (ESI) m/z: 246 ([M+H]$^+$).

EXAMPLE II.4 exo-3-(3-Isopropylphenoxy)-9-azabicyclo[3.3.1]nonane

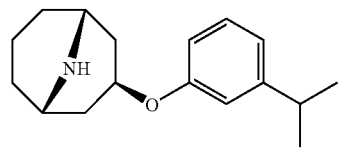

MS (ESI) m/z: 260 ([M+H]$^+$).

EXAMPLE II.5 exo-3-(4-Bromophenoxy)-9-azabicyclo[3.3.1]nonane

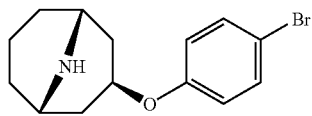

MS (ESI) m/z: 297 ([M+H]$^+$).

EXAMPLE II.6 exo-3-(4-Chloro-3-trifluoromethylphenoxy)-9-azabicyclo[3.3.1]nonane

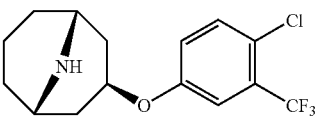

MS (ESI) m/z:320/322 ([M+H]$^+$).

EXAMPLE II.7 exo-4-(9-Azabicyclo[3.3.1]non-3-yloxy)-2-chlorobenzonitrile

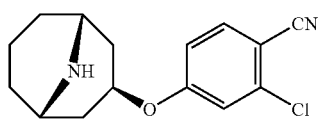

MS (ESI) m/z:277/279 ([M+H]$^+$).

EXAMPLE II.8 exo-5-(9-Azabicyclo[3.3.1]non-3-yloxy)-2-bromobenzonitrile

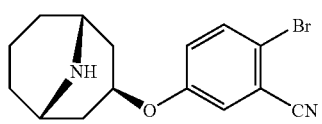

Prepared from 2-bromo-5-hydroxybenzonitrile (prepared as described in *J. Org. Chem.*, 1997, 62, 4504). MS (ESI) m/z: 322 ([M+H]$^+$).

EXAMPLE II.9 exo-3-(4-Chloro-3,5-dimethylphenoxy)-9-azabicyclo[3.3.1]nonane

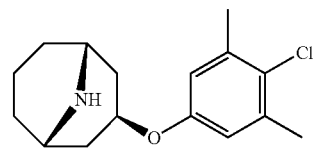

MS (ESI) m/z:280/282 ([M+H]$^+$).

EXAMPLE II.10 exo-3-(3,4,5-Trimethyphenoxy)-9-azabicyclo[3.3.1]nonane

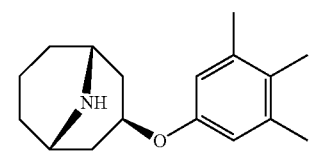

MS (ESI) m/z: 260 ([M+H]$^+$).

EXAMPLE II.11 exo-3-(3,5-Dibromo-4-methylphenoxy)-9-azabicyclo[3.3.1]nonane

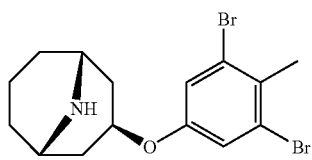

MS (ESI) m/z: 390 ([M+H]$^+$).

EXAMPLE II.12 exo-3-(3-Fluorophenoxy)-9-azabicyclo[3.3.1]nonane

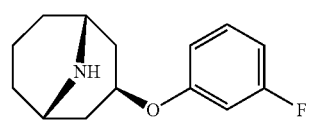

MS (ESI) m/z: 236 ([M+H]$^+$).

EXAMPLE II.13 exo-3-(3-Methylphenoxy)-9-azabicyclo[3.3.1]nonane

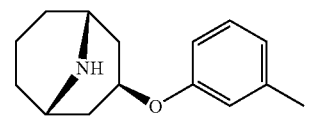

MS (ESI) m/z: 232 ([M+H]$^+$).

EXAMPLE II.14 exo-3-(3-Propylphenoxy)-9-azabicyclo[3.3.1]nonane

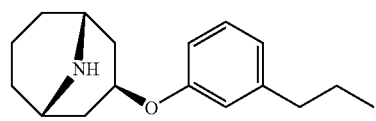

MS (ESI) m/z: 260 ([M+H]$^+$).

EXAMPLE II.15 exo-3-(3-Bromo-4-methylphenoxy)-9-azabicyclo[3.3.1]nonane

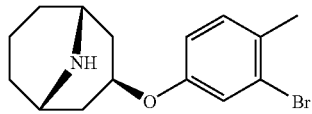

Prepared from 3-bromo-4-methylphenol. MS (ESI) m/z: 311 ([M+H]⁺).

EXAMPLE II.16 exo-3-(2-Methoxyphenoxy)-9-azabicyclo[3.3.1]nonane

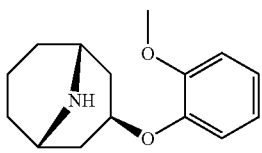

MS (ESI) m/z: 248 ([M+H]⁺).

EXAMPLE II.17 exo-3-(4-Chlorophenoxy)-9-azabicyclo[3.3.1]nonane

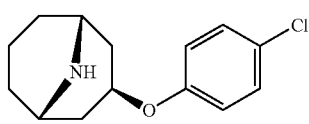

MS (ESI) m/z: 252/254 ([M+H]⁺).

EXAMPLE II.18 exo-3-(4-Chloro-3-fluorophenoxy)-9-azabicyclo[3.3.1]nonane

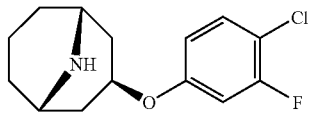

MS (ESI) m/z: 270/272 ([M+H]⁺).

EXAMPLE II.19 exo-3-(2,3,5-Trichlorophenoxy)-9-azabicyclo[3.3.1]nonane

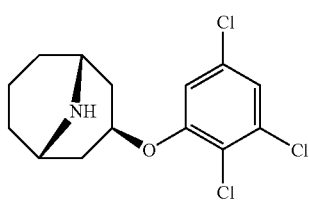

MS (ESI) m/z: 320 ([M+H]⁺).

EXAMPLE II.20 exo-3-(2-Trifluoromethylphenoxy)-9-azabicyclo[3.3.1]nonane

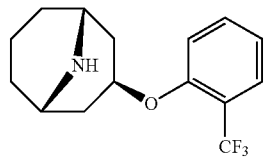

MS (ESI) m/z: 286 ([M+H]⁺).

EXAMPLE II.21 exo-3-(4-Trifluoromethylphenoxy)-9-azabicyclo[3.3.1]nonane

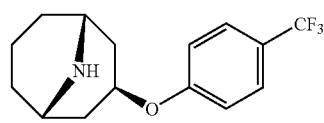

MS (ESI) m/z: 286 ([M+H]⁺).

EXAMPLE II.22 exo-3-(3-Nitrophenoxy)-9-azabicyclo[3.3.1]nonane

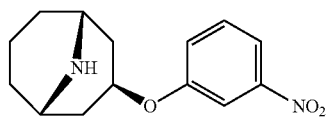

MS (ESI) m/z: 263 ([M+H]⁺).

EXAMPLE II.23 exo-3-(3,4-Dimethylphenoxy)-9-azabicyclo[3.3.1]nonane

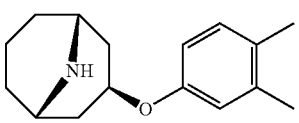

MS (ESI) m/z: 246 ([M+H]⁺).

EXAMPLE II.24 exo-3-(2-Trifluoromethoxyphenoxy)-9-azabicyclo[3.3.1]nonane

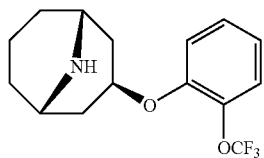

MS (ESI) m/z: 302 ([M+H]⁺).

EXAMPLE II.25 exo-3-(3-Trifluoromethoxyphenoxy)-9-azabicyclo[3.3.1]nonane

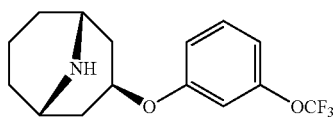

MS (ESI) m/z: 302 ([M+H]⁺).

EXAMPLE II.26 exo-3-(3-Trifluoromethylphenoxy)-9-azabicyclo[3.3.1]nonane

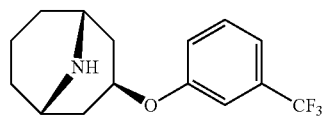

MS (ESI) m/z: 286 ([M+H]⁺).

EXAMPLE II.27 exo-3-(2-Chlorophenoxy)-9-azabicyclo[3.3.1]nonane

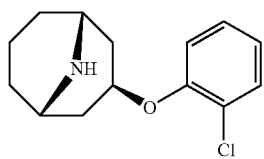

MS (ESI) m/z:252/254 ([M+H]⁺).

EXAMPLE II.28 exo-3-(2,3-Difluorophenoxy)-9-azabicyclo[3.3.1]nonane

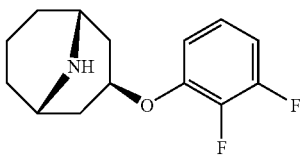

MS (ESI) m/z: 254 ([M+H]⁺).

EXAMPLE II.29 exo-3-(2-Fluorophenoxy)-9-azabicyclo[3.3.1]nonane

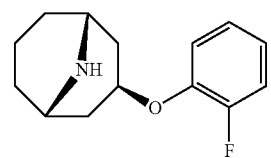

MS (ESI) m/z: 236 ([M+H]⁺).

EXAMPLE II.30 exo-3-(2-Chloro-3-trifluoromethylphenoxy)-9-azabicyclo[3.3.1]nonane

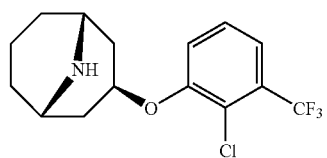

MS (ESI) m/z:320/322 ([M+H]⁺).

EXAMPLE II.31 exo-3-(Benzo[1,3]dioxol-5-yloxy)-9-azabicyclo[3.3.1]nonane

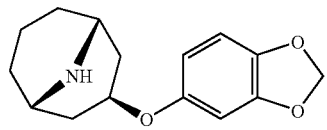

MS (ESI) m/z: 262 ([M+H]⁺).

EXAMPLE II.32 exo-3-(2,5-Dichlorophenoxy)-9-azabicyclo[3.3.1]nonane

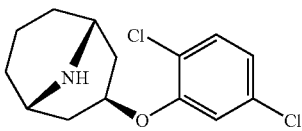

MS (ESI) m/z: 286 ([M+H]+).

EXAMPLE II.33 exo-3-(Benz[b]thiophen-7-yloxy)-9-azabicyclo[3.3.1]nonane

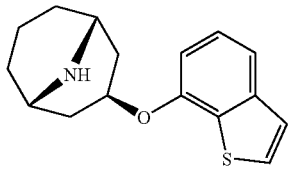

Prepared from benz[b]thiophen-7-ol (prepared as described in *J. Chem. Soc. (Perkin Trans. 1)*, 1993, 2973). MS (ESI) m/z: 274 ([M+H]+).

EXAMPLE II.34 exo-3-(Benz[b]thiophen-5-yloxy)-9-azabicyclo[3.3.1]nonane

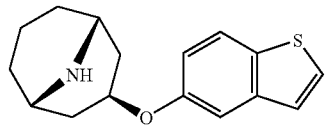

Prepared from benz[b]thiophen-5-ol (prepared as described in *Synth. Comm.*, 1991, 21(7), 959-964. MS (ESI) m/z: 274 ([M+H]+).

EXAMPLE II.35 exo-3-(Benz[b]thiophen-6-yloxy)-9-azabicyclo[3.3.1]nonane

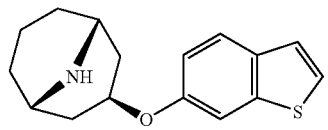

Prepared from benz[b]thiophen-6-ol. MS (ESI) m/z: 274 ([M+H]+).

EXAMPLE II.36 exo-3-(Benzo[b]thiophen-4-yloxy)-9-azabicyclo[3.3.1]nonane

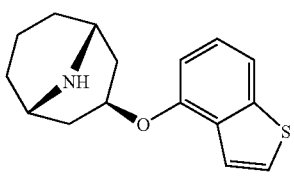

Prepared from benzo[b]thiophen-4-ol (prepared as described in *J. Chem. Res.*, 1993, 192). MS (ESI) m/z: 274 ([M+H]+).

EXAMPLE II.37 exo-3-(4-Fluorobenzo[b]thiophen-7-yloxy)-9-azabicyclo[3.3.1]nonane

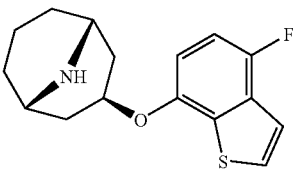

Prepared from 4-fluorobenzo[b]thiophen-7-ol (prepared as described in WO 04/043904). MS (ESI) m/z: 292 ([M+H]+).

EXAMPLE II.38 exo-3-(4-Chlorobenzo[b]thiophen-7-yloxy)-9-azabicyclo[3.3.1]nonane

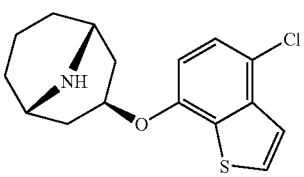

Prepared from 4-chlorobenzo[b]thiophen-7-ol. MS (ESI) m/z: 308/310 ([M+H]+).

EXAMPLE II.39 exo-3-(4-Fluoro-3-methylbenzo[b]thiophen-7-yloxy)-9-azabicyclo[3.3.1]nonane

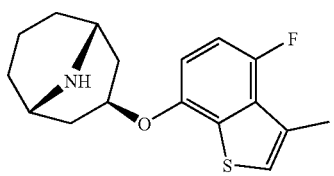

Prepared from 4-fluoro-3-methylbenzo[b]thiophen-7-ol (prepared as described in WO 04/043904). MS (ESI) m/z: 306 ([M+H]$^+$).

EXAMPLE II.40 exo-3-(3-Bromobenzo[b]thiophen-4-yloxy)-9-azabicyclo[3.3.1]nonane

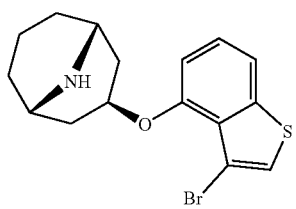

Prepared from 3-bromobenzo[b]thiophen-4-ol (prepared as described in WO 04/043904). MS (ESI) m/z: 353 ([M+H]$^+$).

EXAMPLE II.41 exo-3-(7-Fluorobenzo[b]thiophen-4-yloxy)-9-azabicyclo[3.3.1]nonane

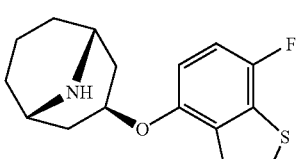

Prepared from 7-fluorobenzo[b]thiophen-4-ol (prepared as described in WO 04/043904). MS (ESI) m/z: 292 ([M+H]$^+$).

EXAMPLE II.42 exo-3-(Benzo[b]furan-7-yloxy)-9-azabicyclo[3.3.1]nonane

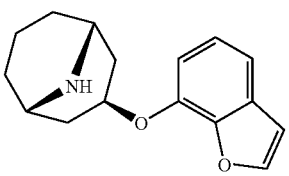

Prepared from benzo[b]furan-7-ol (prepared from 7-methoxybenzo[b]furan according to a similar demethylation method as described in WO 04/043904). MS (ESI) m/z: 258 ([M+H]$^+$).

EXAMPLE II.43 exo-3-(Benzo[b]furan-4-yloxy)-9-azabicyclo[3.3.1]nonane

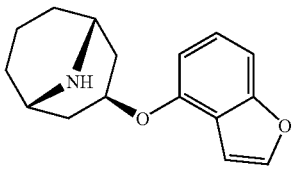

Prepared from benzo[b]furan-4-ol (prepared according to the method described in SYNLETT, 1997, 1163). MS (ESI) m/z: 258 ([M+H]$^+$).

EXAMPLE II.44 exo-3-(Benzo[b]furan-5-yloxy)-9-azabicyclo[3.3.1]nonane

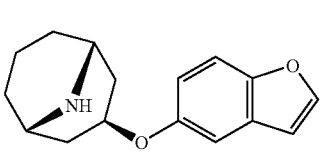

Prepared from benzo[b]furan-5-ol (prepared from 5-methoxybenzo[b]furan according to a similar demethylation method as described in WO 04/043904). MS (ESI) m/z: 258 ([M+H]$^+$).

EXAMPLE II.45 exo-3-(Benzofuran-6-yloxy)-9-azabicyclo[3.3.1]nonane

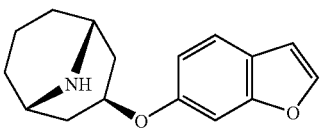

Prepared from benzo[b]furan-6-ol (prepared according to the method described in SYNLETT, 1997, 1163). MS (ESI) m/z: 258 ([M+H]$^+$).

EXAMPLE II.46 exo-3-(4,5-Dichloropyridin-2-yloxy)-9-azabicyclo[3.3.1]nonane

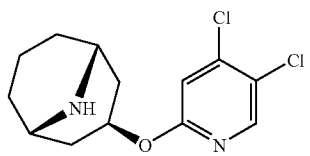

Prepared from 4,5-dichloro-2-hydroxypyridine (prepared as described in Recl. Trav. Chim. Pays-Bas, 1953, 72, 285). MS (ESI) m/z:287/289 ([M+H]$^+$).

EXAMPLE II.47 exo-3-(3,4-Dichloropyridin-2-yloxy)-9-azabicyclo[3.3.1]nonane

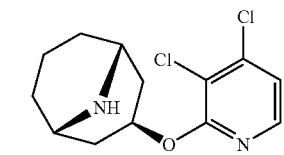

Prepared from 3,4-dichloro-2-hydroxypyridine. MS (ESI) m/z: 287 ([M+H]$^+$).

EXAMPLE II.48 exo-3-(5,6-Dichloropyridin-2-yloxy)-9-azabicyclo[3.3.1]nonane

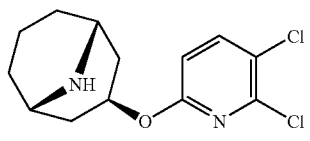

Prepared from 2,3-dichloro-6-hydroxypyridine. MS (ESI) m/z: 287 ([M+H]$^+$).

EXAMPLE II.49 exo-3-(4,6-Dichloropyridin-2-yloxy)-9-azabicyclo[3.3.1]nonane

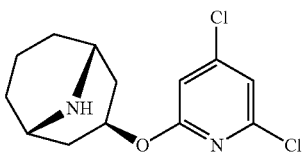

Prepared from 2,4-dichloro-6-hydroxypyridine. MS (ESI) m/z: 287 ([M+H]$^+$).

EXAMPLE II.50 exo-3-(5-Bromopyridin-2-yloxy)-9-azabicyclo[3.3.1]nonane

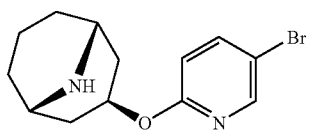

MS (ESI) m/z:297/299 ([M+H]$^+$).

EXAMPLE II.51 exo-3-(6-Chloropyridin-2-yloxy)-9-azabicyclo[3.3.1]nonane

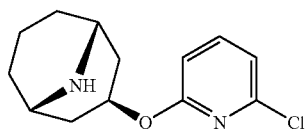

MS (ESI) m/z: 253 ([M+H]$^+$).

EXAMPLE II.52 exo-3-(5-Bromo-4-methylpyridin-2-yloxy)-9-azabicyclo[3.3.1]nonane

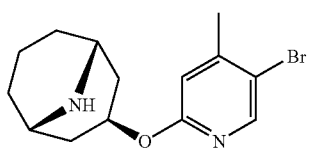

MS (ESI) m/z: 313 ([M+H]$^+$).

EXAMPLE II.53 exo-3-(4-Bromo-5-fluoropyridin-2-yloxy)-9-azabicyclo[3.3.1]nonane

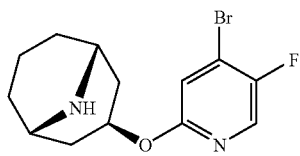

MS (ESI) m/z: 317 ([M+H]⁺).

EXAMPLE II.54 exo-3-(4-Chloropyridin-2-yloxy)-9-azabicyclo[3.3.1]nonane

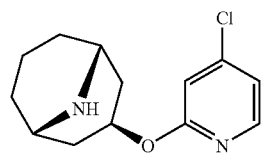

MS (ESI) m/z: 253 ([M+H]⁺).

EXAMPLE II.55 exo-3-(6-Bromopyridin-2-yloxy)-9-azabicyclo[3.3.1]nonane

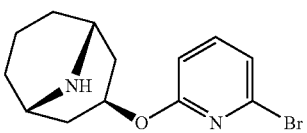

MS (ESI) m/z: 297/299 ([M+H]⁺).

EXAMPLE II.56 exo-2-(9-Azabicyclo[3.3.1]non-3-yloxy)isonicotinonitrile

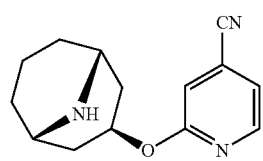

MS (ESI) m/z: 244 ([M+H]⁺).

EXAMPLE II.57 exo-3-(5-Chloropyridin-3-yloxy)-9-azabicyclo[3.3.1]nonane

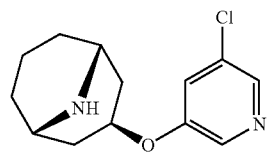

MS (ESI) m/z: 253 ([M+H]⁺).

EXAMPLE II.58 exo-3-(6-Methylpyridin-3-yloxy)-9-azabicyclo[3.3.1]nonane

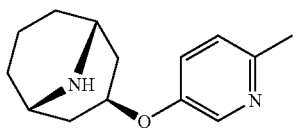

MS (ESI) m/z: 233 ([M+H]⁺).

EXAMPLE II.59 exo-3-(9-Azabicyclo[3.3.1]non-3-yloxy)quinoline

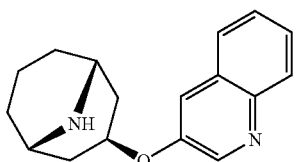

MS (ESI) m/z: 269 ([M+H]⁺).

EXAMPLE II.60 exo-6-(9-Azabicyclo[3.3.1]non-3-yloxy)isoquinoline

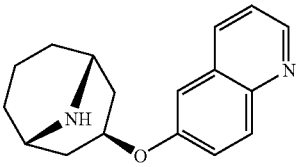

MS (ESI) m/z: 269 ([M+H]⁺).

EXAMPLE II.61 exo-3-(5,6-Dimethoxynaphthalen-1-yloxy)-9-azabicyclo[3.3.1]nonane

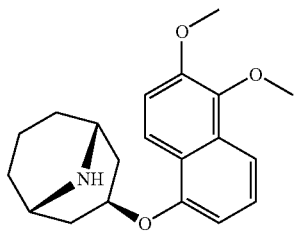

Prepared from 5,6-dimethoxynaphthalen-1-ol (prepared according to the method described in *J. Org. Chem.*, 1995, 60(5), 1267). MS (ESI) m/z: 328 ([M+H]$^+$).

EXAMPLE II.62 exo-3-(5-Bromonaphthalen-1-yloxy)-9-azabicyclo[3.3.1]nonane

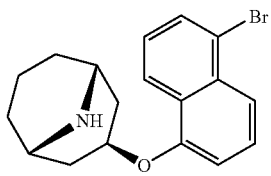

Prepared from 5-bromonaphthalen-1-ol (prepared according to the method described in *J. Org. Chem.*, 1991, 56(23), 6704). MS (ESI) m/z: 347 ([M+H]$^+$).

EXAMPLE II.63 exo-3-(7-Methoxynaphthalen-2-yloxy)-9-azabicyclo[3.3.1]nonane

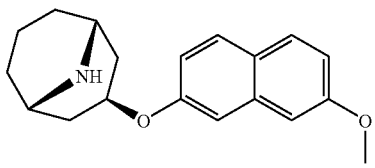

MS (ESI) m/z: 298 ([M+H]$^+$).

EXAMPLE II.64 exo-3-(6-Methoxynaphthalen-2-yloxy)-9-azabicyclo[3.3.1]nonane

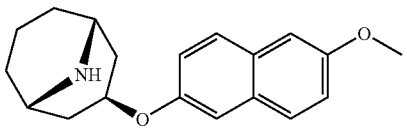

MS (ESI) m/z: 298 ([M+H]$^+$).

EXAMPLE II.65 exo-4-(9-Azabicyclo[3.3.1]non-3-yloxy)naphthalen-2-ol

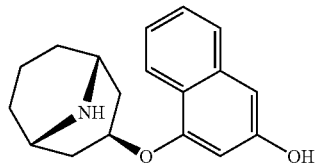

MS (ESI) m/z: 284 ([M+H]$^+$).

EXAMPLE II.66 exo-8-(9-Azabicyclo[3.3.1]non-3-yloxy)naphthalen-2-ol

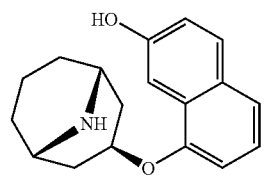

MS (ESI) m/z: 284 ([M+H]$^+$).

EXAMPLE II.67 exo-3-(9-Azabicyclo[3.3.1]non-3-yloxy)naphthalen-1-ol

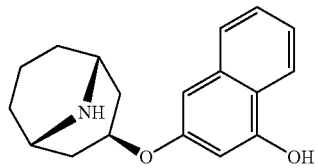

MS (ESI) m/z: 284 ([M+H]$^+$).

EXAMPLE II.68 exo-4-(9-Azabicyclo[3.3.1]non-3-yloxy)phenol

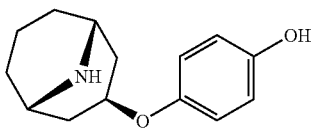

MS (ESI) m/z: 234 ([M+H]$^+$).

EXAMPLE II.69 exo-3-(Biphenyl-3-yloxy)-9-azabicyclo[3.3.1]nonane

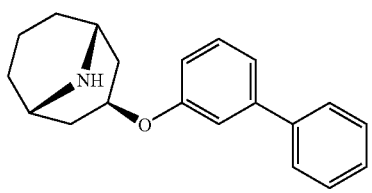

MS (ESI) m/z: 294 ([M+H]$^+$).

Procedure III

EXAMPLE III.1 endo-3-(3-Bromo-2-methylphenoxy)-9-azabicyclo[3.3.1]nonane

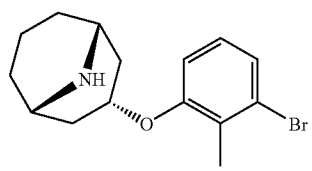

Exo-3-hydroxy-9-azabicyclo[3.3.1]nonane-9-carboxylic acid tert-butyl ester (100 mg, 0.41 mmol), (4,4-dimethyl-1,1-dioxido-1,2,5-thiadiazolidin-2-yl)triphenyl phosphonium (prepared as described in *J. Org. Chem.*, 1994, 59, 2289) (225 mg, 0.62 mmol) and 3-bromo-2-methylphenol (116 mg, 0.62 mmol) were dissolved in dichloromethane (3 mL). The reaction mixture was stirred at ambient temperature for 4 h followed by addition of trifluoroacetic acid (2 mL). Stirring was continued for 12 h. Volatiles were evaporated under reduced pressure, the residue dissolved in methanol (1 mL) and passed through an SCX cartridge (primed with dilute TFA/methanol), washed with methanol, then the product was eluted with a solution of 2M ammonia in methanol. The product was further purified by preparative reverse phase LCMS to afford endo-3-(3-bromo-2-methylphenoxy)-9-azabicyclo[3.3.1]nonane trifluoroacetic acid salt (14.4 mg, 8%).

Data for endo-3-(3-bromo-2-methylphenoxy)-9-azabicyclo[3.3.1]nonane trifluoroacetic acid salt:

MS (ESI) m/z: 310 ([M+H]$^+$).

Similarly prepared were:

EXAMPLE III.2 endo-3-(2-Chlorophenoxy)-9-azabicyclo[3.3.1]nonane

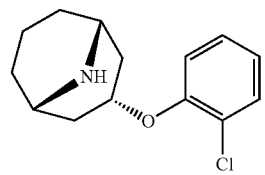

MS (ESI) m/z: 252/254 ([M+H]$^+$).

EXAMPLE III.3 endo-3-(3-Chlorophenoxy)-9-azabicyclo[3.3.1]nonane

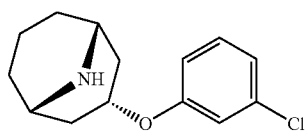

MS (ESI) m/z: 252/254 ([M+H]$^+$).

EXAMPLE III.4 endo-3-(4-Chlorophenoxy)-9-azabicyclo[3.3.1]nonane

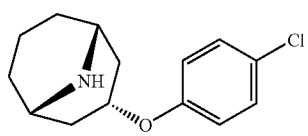

MS (ESI) m/z: 252/254 ([M+H]$^+$).

EXAMPLE III.5 endo-3-(2,3-Dichlorophenoxy)-9-azabicyclo[3.3.1]nonane

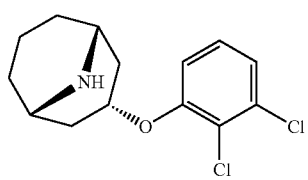

MS (ESI) m/z: 286 ([M+H]$^+$).

EXAMPLE III.6 endo-3-(3,4-Dichlorophenoxy)-9-azabicyclo[3.3.1]nonane

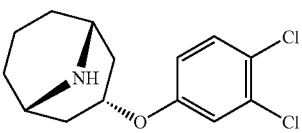

MS (ESI) m/z: 286 ([M+H]$^+$).

EXAMPLE III.7 endo-3-(3,5-Dimethylphenoxy)-9-azabicyclo[3.3.1]nonane

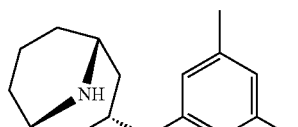

MS (ESI) m/z: 246 ([M+H]$^+$).

EXAMPLE III.8 endo-3-(3-Bromophenoxy)-9-azabicyclo[3.3.1]nonane

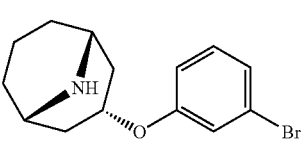

MS (ESI) m/z: 297 ([M+H]$^+$).

EXAMPLE III.9 endo-3-(3-Methoxyphenoxy)-9-azabicyclo[3.3.1]nonane

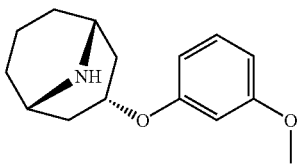

MS (ESI) m/z: 248 ([M+H]$^+$).

EXAMPLE III.10 endo-3-(3-Fluorophenoxy)-9-azabicyclo[3.3.1]nonane

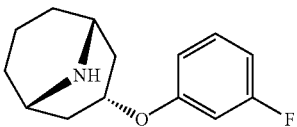

MS (ESI) m/z: 236 ([M+H]$^+$).

EXAMPLE III.11 endo-3-(4-Methylphenoxy)-9-azabicyclo[3.3.1]nonane

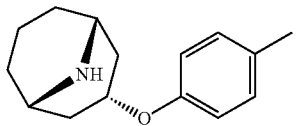

MS (ESI) m/z: 232 ([M+H]$^+$).

EXAMPLE III.12 endo-3-(2,3-Difluorophenoxy)-9-azabicyclo[3.3.1]nonane

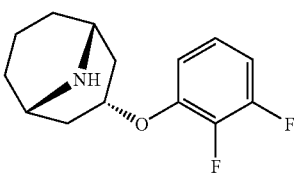

MS (ESI) m/z: 254 ([M+H]$^+$).

EXAMPLE III.13 endo-3-(3-Chloro-4-fluorophenoxy)-9-azabicyclo[3.3.1]nonane

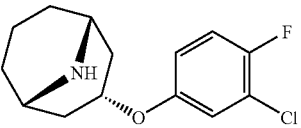

MS (ESI) m/z: 270 ([M+H]$^+$).

EXAMPLE III.14 endo-3-(9-Azabicyclo[3.3.1]non-3-yloxy)benzonitrile

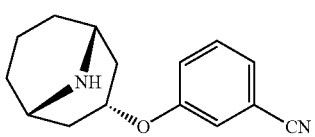

MS (ESI) m/z: 243 ([M+H]$^+$).

EXAMPLE III.15 endo-3-(4-Chloro-3-methylphenoxy)-9-azabicyclo[3.3.1]nonane

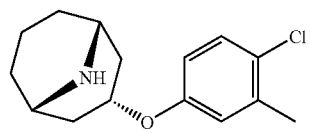

MS (ESI) m/z: 266/268 ([M+H]$^+$).

EXAMPLE III.16 endo-3-(3,5-Dichlorophenoxy)-9-azabicyclo[3.3.1]nonane

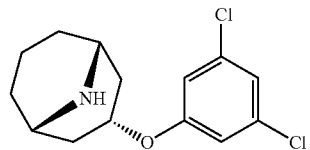

MS (ESI) m/z: 286 ([M+H]$^+$).

EXAMPLE III.17 endo-3-(2,3,5-Trichlorophenoxy)-9-azabicyclo[3.3.1]nonane

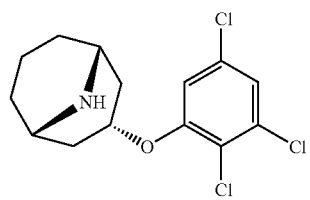

MS (ESI) m/z: 320 ([M+H]$^+$).

EXAMPLE III.18 endo-3-(3-Phenoxyphenoxy)-9-azabicyclo[3.3.1]nonane

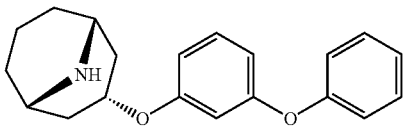

MS (ESI) m/z: 310 ([M+H]$^+$).

EXAMPLE III.19 endo-3-Phenoxy-9-azabicyclo[3.3.1]nonane

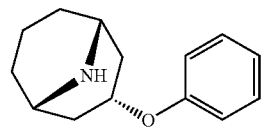

MS (ESI) m/z: 218 ([M+H]$^+$).

EXAMPLE III.20 endo-3-(2,3-Dimethylphenoxy)-9-azabicyclo[3.3.1]nonane

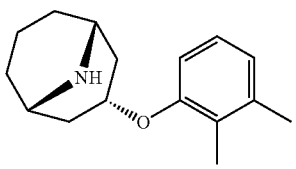

MS (ESI) m/z: 246 ([M+H]$^+$).

Procedure IV

EXAMPLE IV.1 exo-3-(3-Fluoro-4-methylphenoxy)-9-azabicyclo[3.3.1]nonane

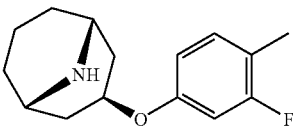

Diethylazodicarboxylate (87 mg, 78 µL, 0.497 mmol) was added dropwise to a solution of endo-3-hydroxy-9-aza-bicyclo[3.3.1]nonane-9-carboxylic acid tert-butyl ester (100 mg, 0.414 mmol), triphenylphosphine (130 mg, 0.497 mmol) and 3-fluoro-4-methylphenol (63 mg, 0.497 mmol) in THF (4 mL). The reaction mixture was stirred under a nitrogen atmosphere for 12 h at ambient temperature. Volatiles were removed under reduced pressure. The resultant oil was dissolved in dichloromethane (2 mL), trifluoroacetic acid (1 mL) added and the reaction mixture stirred at room temperature for 12 h. Volatiles were removed under reduced pressure, the crude product dissolved in methanol (4 mL) and the solution loaded onto a SCX cartridge (Phenomenex). The cartridge was eluted with methanol (20 mL) to remove triphenylphosphine oxide followed by elution with ammonia in methanol (2 M, 20 mL). Evaporation in vacuo afforded the crude product which was further purified by preparative reverse phase LCMS to afford exo-3-(3-fluoro-4-methylphenoxy)-9-azabicyclo[3.3.1]nonane trifluoroacetic acid salt (17 mg, 11%).

Data for exo-3-(3-fluoro-4-methylphenoxy)-9-azabicyclo[3.3.1]nonane trifluoroacetic acid salt:

MS (ESI) m/z: 250 ([M+H]$^+$).

Similarly prepared were:

EXAMPLE IV.2 exo-3-(3,4-Dichlorophenoxy)-9-azabicyclo[3.3.1]nonane

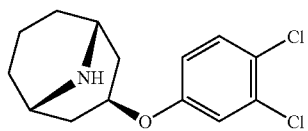

MS (ESI) m/z: 286 ([M+H]$^+$).

EXAMPLE IV.3 exo-3-(3-Phenoxyphenoxy)-9-azabicyclo[3.3.1]nonane

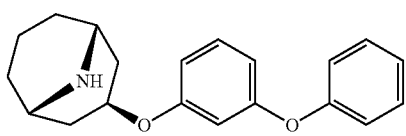

MS (ESI) m/z: 310 ([M+H]$^+$).

EXAMPLE IV.4 exo-3-(3-Phenethyloxyphenoxy)-9-azabicyclo[3.3.1]nonane

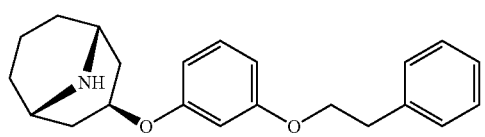

Prepared from 3-phenethyloxyphenol (prepared according to the method described in *SYNLETT*, 2003, 7, 997). MS (ESI) m/z: 338 ([M+H]$^+$).

EXAMPLE IV.5 exo-3-(2,3-Dichlorophenoxy)-9-azabicyclo[3.3.1]nonane

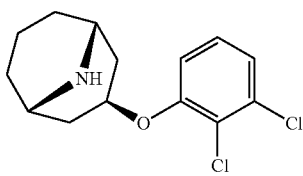

MS (ESI) m/z: 286 ([M+H]$^+$).

EXAMPLE IV.6 exo-3-(3-Bromophenoxy)-9-azabicyclo[3.3.1]nonane

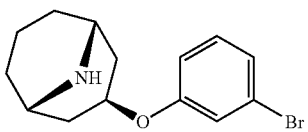

MS (ESI) m/z: 297 ([M+H]$^+$).

EXAMPLE IV.7 exo-3-(9-Azabicyclo[3.3.1]non-3-yloxy)benzonitrile

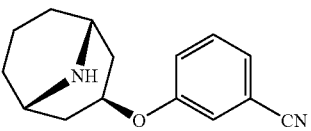

MS (ESI) m/z: 243 ([M+H]$^+$).

EXAMPLE IV.8 exo-3-(3-Methyl-5-trifluoromethylphenoxy)-9-azabicyclo[3.3.1]nonane

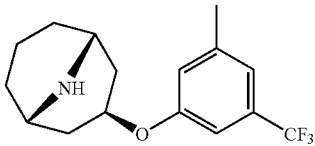

Prepared from 3-methyl-5-trifluoromethylphenol. MS (ESI) m/z: 300 ([M+H]⁺).

EXAMPLE IV.9 exo-3-(4-Chloro-3-trifluoromethylphenoxy)-9-azabicyclo[3.3.1]nonane

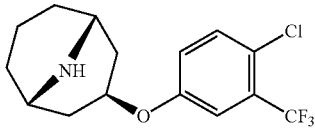

Prepared from 4-chloro-3-trifluoromethylphenol. MS (ESI) m/z: 320 ([M+H]⁺).

EXAMPLE IV.10 exo-3-(2-Methyl-3-trifluoromethylphenoxy)-9-azabicyclo[3.3.1]nonane

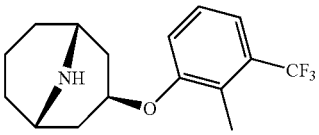

Prepared from 2-methyl-3-trifluoromethylphenol. MS (ESI) m/z: 300 ([M+H]⁺).

EXAMPLE IV.11 exo-3-(3-Chloro-2-methylphenoxy)-9-azabicyclo[3.3.1]nonane

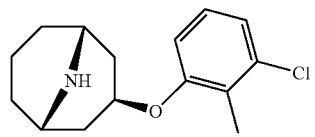

Prepared from 3-chloro-2-methylphenol. MS (ESI) m/z: 266/268 ([M+H]⁺).

EXAMPLE IV.12 exo-3-(2-Bromo-3-chlorophenoxy)-9-azabicyclo[3.3.1]nonane

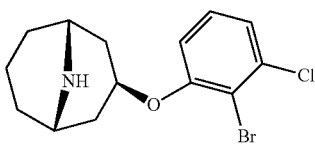

MS (ESI) m/z: 331 ([M+H]⁺).

EXAMPLE IV.13 exo-3-(3-Fluoro-2-methylphenoxy)-9-azabicyclo[3.3.1]nonane

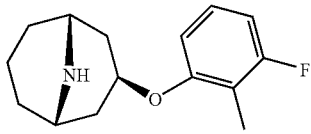

Prepared from 3-fluoro-2-methylphenol. MS (ESI) m/z: 250 ([M+H]⁺).

EXAMPLE IV.14 exo-3-(4-Chloro-3-methylphenoxy)-9-azabicyclo[3.3.1]nonane

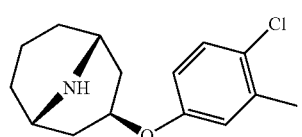

MS (ESI) m/z: 266/268 ([M+H]⁺).

EXAMPLE IV.15 exo-3-(4-Chloro-3-ethylphenoxy)-9-azabicyclo[3.3.1]nonane

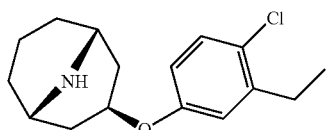

MS (ESI) m/z: 280/282 ([M+H]⁺).

EXAMPLE IV.16 exo-3-(3,4-Difluorophenoxy)-9-azabicyclo[3.3.1]nonane

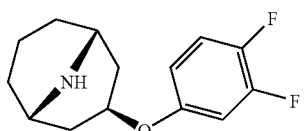

MS (ESI) m/z: 254 ([M+H])⁺).

EXAMPLE IV.17 exo-3-(3-Chloro-4-fluorophenoxy)-9-azabicyclo[3.3.1]nonane

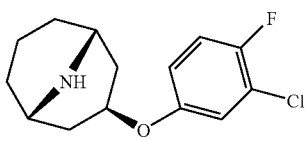

MS (ESI) m/z: 270 ([M+H]$^+$).

EXAMPLE IV.18 exo-3-(4-Fluoro-3-methylphenoxy)-9-azabicyclo[3.3.1]nonane

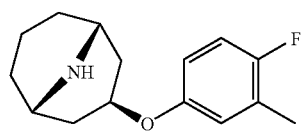

MS (ESI) m/z: 250 ([M+H]$^+$).

EXAMPLE IV.19 exo-3-(3-Chloro-4-methylphenoxy)-9-azabicyclo[3.3.1]nonane

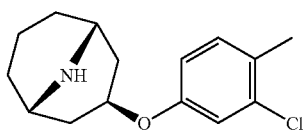

MS (ESI) m/z: 266/268 ([M+H]$^+$).

EXAMPLE IV.20 exo-3-(3,5-Dibromophenoxy)-9-azabicyclo[3.3.1]nonane

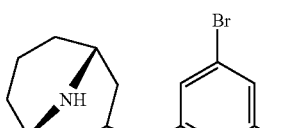

Prepared from 3,5-dibromophenol. MS (ESI) m/z: 376 ([M+H]$^+$)

EXAMPLE IV.21 exo-3-(3,5-Difluorophenoxy)-9-azabicyclo[3.3.1]nonane

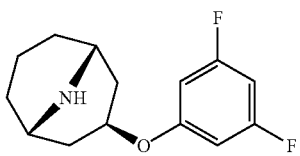

MS (ESI) m/z: 254 ([M+H]$^+$).

EXAMPLE IV.22 exo-3-(3-Bromo-2-methylphenoxy)-9-azabicyclo[3.3.1]nonane

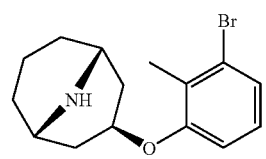

Prepared from 3-bromo-2-methylphenol (prepared according to the method described in *Synth. Comm.,* 1991, 21, 959-964). MS (ESI) m/z: 311 ([M+H]$^+$).

EXAMPLE IV.23 exo-3-(3,4-Dichloro-2-fluorophenoxy)-9-azabicyclo[3.3.1]nonane

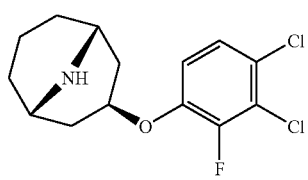

Prepared from 3,4-dichloro-2-fluorophenol. MS (ESI) m/z: 304 ([M+H]$^+$).

EXAMPLE IV.24 exo-3-(3,4-Dichloro-2-methylphenoxy)-9-azabicyclo[3.3.1]nonane

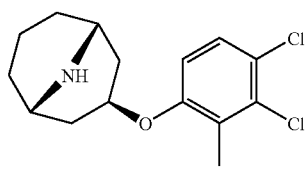

Prepared from 3,4-dichloro-2-methylphenol (prepared according to the method described in *Tetrahedron*, 1998, 54(12), 2953). MS (ESI) m/z: 300 ([M+H]$^+$).

EXAMPLE IV.25 exo-3-(2,3-Dichloro-4-fluorophenoxy)-9-azabicyclo[3.3.1]nonane

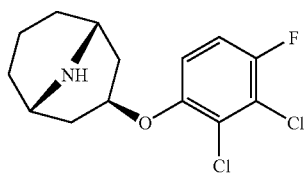

Prepared from 2,3-dichloro-4-fluorophenol. MS (ESI) m/z: 304 ([M+H]$^+$).

EXAMPLE IV.26 exo-3-Phenoxy-9-azabicyclo[3.3.1]nonane

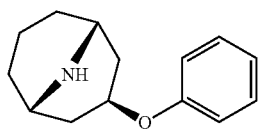

MS (ESI) m/z: 218 ([M+H]$^+$).

EXAMPLE IV.27 exo-3-(3,5-Dichlorophenoxy)-9-azabicyclo[3.3.1]nonane

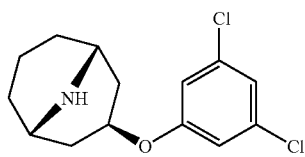

MS (ESI) m/z: 286 ([M+H]$^+$).

EXAMPLE IV.28 exo-3-(3-Iodophenoxy)-9-azabicyclo[3.3.1]nonane

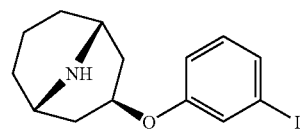

MS (ESI) m/z: 344 ([M+H]$^+$).

EXAMPLE IV.29 exo-3-(3-Chlorophenoxy)-9-azabicyclo[3.3.1]nonane

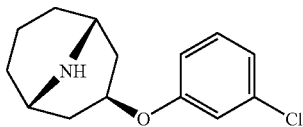

MS (ESI) m/z: 252/254 ([M+H]$^+$).

EXAMPLE IV.30 exo-3-(Naphthalen-1-yloxy)-9-azabicyclo[3.3.1]nonane

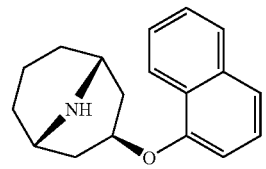

MS (ESI) m/z: 268 ([M+H]$^+$).

EXAMPLE IV.31 exo-3-(Naphthalen-2-yloxy)-9-azabicyclo[3.3.1]nonane

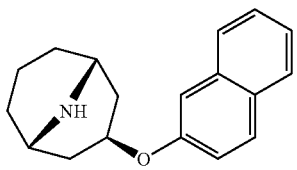

MS (ESI) m/z: 268 ([M+H]$^+$).

EXAMPLE IV.32 exo-3-(7-Methoxynaphthalen-1-yloxy)-9-azabicyclo[3.3.1]nonane

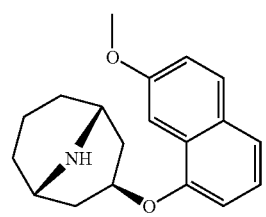

Prepared from 7-methoxynaphthalen-1-ol (prepared according to the method described in *J. Org. Chem.*, 1995, 60(5), 1267). MS (ESI) m/z: 298 ([M+H]$^+$).

EXAMPLE IV.33 exo-3-(3-Methoxynaphthalen-1-yloxy)-9-azabicyclo[3.3.1]nonane

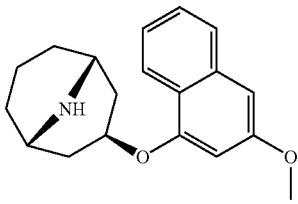

Prepared from 3-methoxynaphthalen-1-ol (prepared as described in *Aust. J. Chem.*, 1993, 46(5), 731). MS (ESI) m/z: 298 ([M+H]$^+$).

Procedure V

EXAMPLE V.1 exo-3-(3-Ethyl-5-methylphenoxy)-9-azabicyclo[3.3.1]nonane a) endo-3-Methanesulfonyloxy-9-azabicyclo[3.3.1]nonane-9-carboxylic acid tert-butyl ester

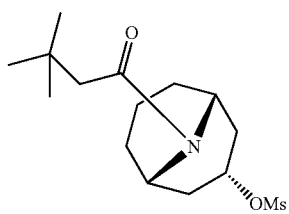

A solution of endo-3-hydroxy-9-azabicyclo[3.3.1]nonane-9-carboxylic acid tert-butyl ester (500 mg, 2.07 mmol) and triethylamine (316 µL, 2.3 mmol) in dichloromethane (15 mL) was cooled to 0° C. under a nitrogen gas atmosphere. Methanesulphonyl chloride (260 mg, 203 mmol) was added dropwise, the reaction mixture allowed to warm to ambient temperature and stirred for 12 h. Dichloromethane was evaporated under reduced pressure. The crude product was crystallised from heptane to afford the title compound (623 mg, 85%) as a white solid.

Data for endo-3-methanesulfonyloxy-9-azabicyclo[3.3.1]nonane-9-carboxylic acid tert-butyl ester MS (ESI) m/z: 220 ([MH-Boc]$^+$).

b) exo-3-(3-Ethyl-5-methylphenoxy)-9-azabicyclo[3.3.1]nonane

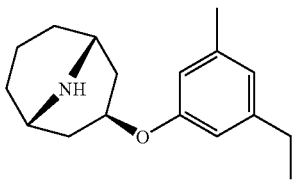

3-Ethyl-5-methylphenol (41 mg, 0.30 mmol) was dissolved in dry DMF (1.5 mL) and purged with nitrogen gas. Sodium hydride (60% suspension in mineral oil, 15 mg, 0.60 mmol) was added and the resulting mixture was stirred at ambient temperature for 30 min. Endo-3-Methanesulfonyloxy-9-azabicyclo[3.3.1]nonane-9-carboxylic acid tert-butyl ester (100 mg, 0.30 mmol) in DMF (0.5 mL) was added and the reaction mixture was stirred at ambient temperature for 12 h. The solvent was evaporated under reduced pressure and the residue treated with a solution of 50% trifluoracetic acid in dichloromethane (3 mL) and stirred for 1 h. The solvent was evaporated in vacuo, the crude product was dissolved in methanol (4 mL) and the solution loaded onto a SCX cartridge (Phenomenex). The cartridge was washed with methanol (20 mL) followed by elution with ammonia in methanol (2 M, 20 mL) to afford the title compound (27 mg, 35%).

Data for exo-3-(3-ethyl-5-methylphenoxy)-9-azabicyclo[3.3.1]nonane: MS (ESI) m/z: 260 ([M+H]$^+$)

Similarly prepared were:

EXAMPLE V.2 exo-3-(3-Isopropyl-5-methylphenoxy)-9-azabicyclo[3.3.1]nonane

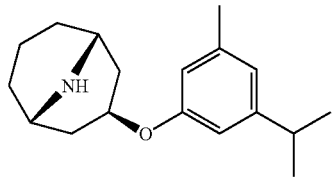

MS (ESI) m/z: 274 ([M+H]$^+$).

EXAMPLE V.3 exo-3-(3,5-Dimethylphenoxy)-9-azabicyclo[3.3.1]nonane

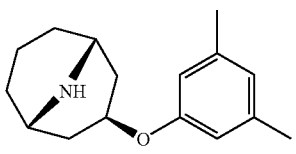

MS (ESI) m/z: 246 ([M+H]$^+$).

EXAMPLE V.4 exo-3-(3,5-Dimethoxyphenoxy)-9-azabicyclo[3.3.1]nonane

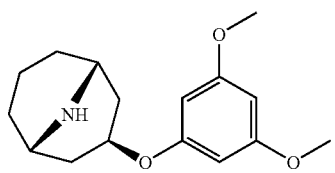

MS (ESI) m/z: 278 ([M+H]+).

Procedure VI

EXAMPLE VI.1 endo-3-(3-Bromophenoxy)-9-methyl-9-azabicyclo[3.3.1]nonane

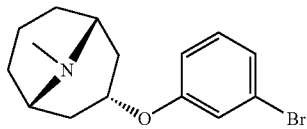

Diethylazodicarboxylate (0.13 mL, 0.82 mmol) was added dropwise to a solution of triphenylphosphine (215 mg, 0.82 mmol), endo-9-methyl-9-azabicyclo[3.3.1]nonan-3-ol (prepared according to the method described in *J. Chem. Soc., (Perkin Trans. 1)*, 1997, 1307) (100 mg, 0.65 mmol) and 3-bromophenol (134 mg, 0.77 mmol) in THF (4 mL). The reaction mixture was stirred under a nitrogen atmosphere for 1 h at room temperature. Volatiles were removed under reduced pressure. The resultant oil was purified by SCX followed by preparative reverse phase HPLC to afford endo-3-(3-bromophenoxy)-9-methyl-9-azabicyclo[3.3.1]nonane trifluoroacetic acid salt (8.3 mg, 4%).

Data for endo-3-(3-bromophenoxy)-9-methyl-9-azabicyclo[3.3.1]nonane trifluoroacetic acid salt:

MS (ESI) m/z: 311 ([M+H]+).

Similarly prepared was:

EXAMPLE VI.2 endo-3-(3,4-Dichlorophenoxy)-9-methyl-9-azabicyclo[3.3.1]nonane

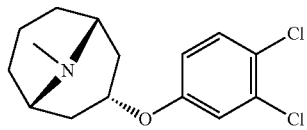

MS (ESI) m/z: 300 ([M+H]+).

Procedure VII

EXAMPLE VII.1 exo-3-(3-Prop-1-ynylphenoxy)-9-azabicyclo[3.3.1]nonane a) exo-3-(3-Iodophenoxy)-9-azabicyclo[3.3.1]nonane-9-carboxylic acid tert-butyl ester

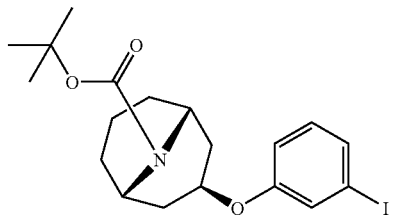

This was repaired according to the procedure described for exo-3-(3-fluoro-4-methylphenoxy)-9-azabicyclo[3.3.1]nonane prior to removal of Boc-protecting group with trifluoroacetic acid.

b) exo-3-(3-Prop-1-ynylphenoxy)-9-azabicyclo[3.3.1]nonane

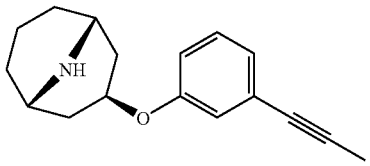

Propyne gas was bubbled through a solution of exo-3-(3-iodophenoxy)-9-azabicyclo[3.3.1]nonane-9-carboxylic acid tert-butyl ester (200 mg, 0.45 mmol), Cl₂Pd(PPh₃)₂ (40 mg), CuI (20 mg), diisopropylamine (1.5 mL) and DMF (0.5 mL) for 20 seconds. The reaction mixture was then heated in a microwave oven at 120° C. for 10 min. The reaction mixture was filtered and the diisopropylamine removed under reduced pressure. The crude product was purified by preparative reverse phase LCMS to yield exo-3-(3-prop-1-ynylphenoxy)-9-azabicyclo[3.3.1]nonane-9-carboxylic acid tert-butyl ester. This was dissolved in dichloromethane (5 mL) and treated with trifluoroacetic acid (1 mL) for 12 h. The product was then purified by preparative reverse phase LCMS yielding exo-3-(3-prop-1-ynylphenoxy)-9-azabicyclo[3.3.1]nonane trifluoroacetic acid salt (34 mg, 20%)

Data for exo-3-(3-prop-1-ynylphenoxy)-9-azabicyclo[3.3.1]nonane trifluoroacetic acid salt: MS (ESI) m/z: 256 ([M+H]+).

Procedure VIII

EXAMPLE VIII.1 exo-3-(3-Ethynylphenoxy)-9-azabicyclo[3.3.1]nonane a) exo-3-(3-Trimethylsilanylethynylphenoxy)-9-azabicyclo[3.3.1]nonane-9-carboxylic acid tert-butyl ester

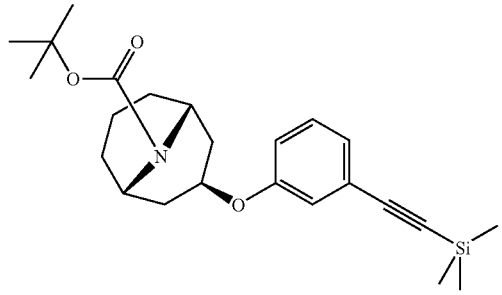

Trimethylsilylacetylene (0.24 mL, 1.72 mmol), exo-3-(3-iodophenoxy)-9-azabicyclo[3.3.1]nonane-9-carboxylic acid tert-butyl ester (633 mg, 1.43 mmol), $Cl_2Pd(PPh_3)_2$ (90 mg), CuI (30 mg), diisopropylamine (4 mL) and DMF (1 mL) were mixed and then heated in a microwave oven at 120° C. for 15 min. The reaction mixture was evaporated and then stirred in a solution of dichloromethane: 10% citric acid (aq.)(10 mL, 1:1 [v/v]). The solution was then passed through a hydrophobic frit and the filtrate purified by chromatography on silica gel with EtOAc:heptane (1:3, v/v) as eluent. This yielded exo-3-(3-trimethylsilanylethynylphenoxy)-9-azabicyclo[3.3.1]nonane-9-carboxylic acid tert-butyl ester as a yellow gum (480 mg, 81%).

Data for exo-3-(3-trimethylsilanylethynylphenoxy)-9-azabicyclo[3.3.1]nonane-9-carboxylic acid tert-butyl ester MS (ESI) m/z: 414 ([M+H]$^+$)

b) exo-3-(3-Ethynylphenoxy)-9-azabicyclo[3.3.1]nonane

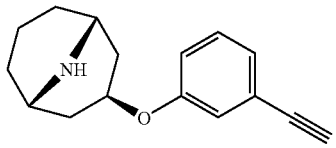

exo-3-(3-Trimethylsilanylethynylphenoxy)-9-azabicyclo[3.3.1]nonane-9-carboxylic acid tert-butyl ester (480 mg, 1.16 mmol) was mixed with methanol (15 mL) and potassium carbonate (200 mg, 1.45 mmol) for 24 h at ambient temperature. The solvent was evaporated under reduced pressure and the residue was stirred with dichloromethane (20 mL) and water (10 mL) and then passed through a hydrophobic frit. The organics were treated with trifluoroacetic acid (5 mL) and stirred for 12 h. On evaporation the crude product was purified by preparative reverse phase LCMS to afford the trifluoroacetic acid salt of the title compound as a white solid (232 mg, 56% 0.65 mmol)

Data for exo-3-(3-ethynylphenoxy)-9-azabicyclo[3.3.1]nonane trifluoroacetic acid salt MS (ESI) m/z: 241 ([M+H]$^+$).

Method IX

EXAMPLE IX.1 exo-3-(3-Bromophenoxy)-9-cyclopropylmethyl-9-azabicyclo[3.3.1]nonane

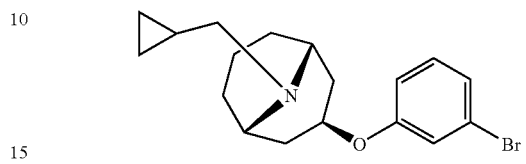

Sodium cyanoborohydride (6.2 mg, 0.099 mmol) was added to a stirred suspension of cyclopropane carboxaldehyde (16.6 µL, 0.099 mmol), exo-3-(3-bromophenoxy)-9-azabicyclo[3.3.1]nonane (28.5 mg, 0.086 mmol) and glacial acetic acid (15 µL) in dry THF (0.5 mL) and the reaction mixture stirred at ambient temperature for 18 h. Methanol (0.5 mL) was added and volatiles evaporated under reduced pressure. The crude product was purified by preparative reverse phase HPLC to afford exo-3-(3-bromophenoxy)-9-cyclopropylmethyl-9-azabicyclo[3.3.1]nonane trifluoroacetic acid salt (27 mg, 68%).

Data for exo-3-(3-bromophenoxy)-9-cyclopropylmethyl-9-azabicyclo[3.3.1]nonane trifluoroacetic acid salt: MS (ESI) m/z: 351 ([M+H]$^+$).

Method X

EXAMPLE X.1 exo-(9-azabicyclo[3.3.1]non-3-yl)(3-chlorophenyl)amine

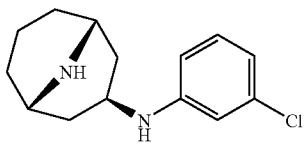

3-Oxa-9-azabicyclo[3.3.1]nonane-9-carboxylic acid tert-butyl ester (200 mg, 0.83 mmol) (prepared from 9-benzyl-9-azabicyclo[3.3.1]nonan-3-one according to methods described for preparation of endo-9-azabicyclo[3.3.1]nonan-3-ol and endo-3-hydroxy-9-azabicyclo[3.3.1]nonane-9-carboxylic acid tert-butyl ester) and 3-chloroaniline (100 mg, 0.80 mmol) were mixed with dichloroethane:acetic acid (2:1 [v/v], 3 mL) and stirred at ambient temperature for 24 h. Sodium cyanoborohydride (100 mg, 1.60 mmol) was added in one portion and stirring continued for 1 h. Sat. $NaHCO_3$ (aq.) (5 mL) was added followed by dichloromethane (20 mL) and the organic phase separated using a hydrophobic frit. The dichloromethane layer was treated with trifluoroacetic acid (2 mL) for 12 h, the product mixture passed through an SCX cartridge (primed with dilute TFA/methanol), washed with methanol, then product eluted with a solution of 2M ammonia in methanol. Further purification by preparative reverse phase HPLC afforded exo-(9-azabicyclo[3.3.1]non-3-yl)(3-chlorophenyl)amine (36 mg, 20%) as the trifluoroacetic acid salt.

Data for exo-(9-azabicyclo[3.3.1]non-3-yl)(3-chlorophenyl)amine trifluoroacetic acid salt: MS (ESI) m/z:251/253 ([M+H]+).

Method XI: Assay of Monoamine Uptake

The in vitro test for the inhibition of dopamine and serotonin uptake was performed in Chinese Hamster Ovary cells expressing the human dopamine transporter (hDAT) or the human serotonin transporter (hSERT). The in vitro test for the inhibition of noradrenaline uptake was performed in Madin Darby Canine Kidney Cells (MDCK) expressing the human noradrenaline transporter (hNET).

Briefly, cell lines stably overexpressing the appropriate human transporter were propagated and plated according to standard cell culture techniques. Following plating, cells were left to adhere for either one or two days. A 6-point serial dilution (normally 1E-5M to 1E-10M) of test and reference compounds was prepared, added to the washed cells and incubated for 5 minutes at room temperature for dopamine or serotonin transporter overexpressing and 37° C. for noradrenaline overexpressing cells. Next, a final concentration of 20 nM of appropriate neurotransmitter (mixture of [$^3$H]-neurotransmitter and non-labelled neurotransmitter) was added and the cells were incubated for three or five minutes at room temperature for dopamine or serotonin transporter overexpressing cells or ten minutes at 37° C. for noradrenaline overexpressing cells. Following termination of the assay, Microscint-20 was added directly to the cells and the amount of radioactivity taken up by the cells was estimated by scintillation counting.

$EC_{50}$ values indicating inhibition of monoamine uptake were calculated using standard curve fitting techniques.

The invention claimed is:

1. A 9-azabicyclo[3.3.1]nonane of formula I,

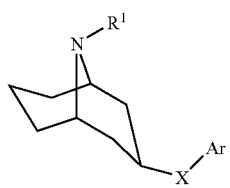

formula I wherein $R^1$ is H or $C_{1-5}$alkyl;

X is O, wherein $R^2$ is H, $C_{1-5}$alkyl or $C_{2-5}$acyl and

Ar is a heteroaryl ring selected from benzothienyl and benzoisothiazolyl, both being optionally substituted with one to three of $R^3$-$R^5$ independently selected from halogen, $C_{1-5}$alkyl, $C_{1-5}$alkoxy, $C_{3-6}$cycloalkyl, $C_{2-5}$alkenyl, $C_{2-5}$alkynyl, CN, $NO_2$, hydroxy, phenyl, phenoxy and phenyl$C_{1-2}$alkoxy, wherein said $C_{1-5}$alkyl and $C_{1-5}$alkoxy are optionally substituted with one to three halogens and wherein said phenyl, phenoxy and phenyl$C_{1-2}$alkoxy are optionally substituted with one to three substituents independently selected from halogen and methyl or two of $R^3$-$R^5$ at adjacent positions together form a methylenedioxy or propylene unit, or a pharmaceutically acceptable salt thereof.

2. The 9-azabicyclo[3.3.1]nonane according to claim h wherein $R^1$ is H or methyl.

3. The 9-azabicyclo[3.3.1]nonane according to claim 1, wherein Ar is benzothienyl optionally substituted with 1-2 substituents independently selected from chloro, fluoro, methyl and cyano.

4. The 9-azabicyclo[3.3.1]nonane according to claim 2, wherein Ar is benzothienyl optionally substituted with 1-2 substituents independently selected from chloro, fluoro, methyl and cyano.

5. A 9-azabicyclo[3.3.1]nonane selected from:
   exo-3-(benzo[d]isothiazol-7-yloxy)-9-azabicyclo[3.3.1] nonane;
   exo-3-(benzo[d]isothiazol-4-yloxy)-9-azabicyclo[3.3.1] nonane;
   exo-3-(3-chloro-2-fluorophenoxy)-9-azabicyclo[3.3.1] nonane;
   exo-3-(benzo[b]thiophen-7-yloxy)-9-azabicyclo[3.3.1] nonane;
   exo-3-(benzo[b]thiophen-6-yloxy)-9-azabicyclo[3.3.1] nonane;
   exo-3-(benzo[b]thiophen-4-yloxy)-9-azabicyclo[3.3.1] nonane;
   exo-3-(3,4-dichloropyridin-2-yloxy)-9-azabicyclo[3.3.1] nonane;
   exo-3-(5,6-dichloropyridin-2-yloxy)-9-azabicyclo[3.3.1] nonane;
   exo-3-(4,6-dichloropyridin-2-yloxy)-9-azabicyclo[3.3.1] nonane;
   exo-3-(3-fluoro-4-methylphenoxy)-9-azabicyclo[3.3.1] nonane;
   exo-3-(2,3-dichlorophenoxy)-9-azabicyclo[3.3.1]nonane;
   exo-3-(9-azabicyclo[3.3.1]non-3 yloxy)benzonitrile;
   exo-3-(3,5-dichlorophenoxy)-9-azabicyclo[3.3.1]nonane and
   exo-3-(3-prop-1-ynylphenoxy)-9-azabicyclo[3.3.1] nonane
   or a pharmaceutically acceptable salt thereof.

6. A pharmaceutical composition comprising a 9-azabicyclo[3.3.1]nonane or a pharmaceutically acceptable salt thereof according to claim 1 in admixture with one or more pharmaceutically acceptable excipients.

7. The 9-azabicyclo[3.3.1]nonane according to claim 1, wherein Ar is benzoisothiazolyl optionally substituted with 1-2 substituents independently selected from chloro, fluoro, methyl and cyano.

8. The 9-azabicyclo[3.3.1]nonane according to claim 2, wherein Ar is benzoisothiazolyl optionally substituted with 1-2 substituents independently selected from chloro, fluoro, methyl and cyano.

* * * * *